(12) United States Patent
Chandy et al.

(10) Patent No.: US 7,378,496 B2
(45) Date of Patent: May 27, 2008

(54) HKCA3/KCNN3 SMALL CONDUCTANCE CALCIUM ACTIVATED POTASSIUM CHANNEL: A DIAGNOSTIC MARKER AND THERAPEUTIC TARGET

(75) Inventors: K. George Chandy, Laguna Beach, CA (US); J. Jay Gargus, Irvine, CA (US); George Gutman, Costa Mesa, CA (US); Emmanuelle Fantino, Tustin, CA (US); Katarin Kalman, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 571 days.

(21) Appl. No.: 10/722,189

(22) Filed: Nov. 24, 2003

(65) Prior Publication Data

US 2004/0137487 A1 Jul. 15, 2004

Related U.S. Application Data

(60) Continuation of application No. 09/565,590, filed on May 4, 2000, now Pat. No. 6,653,100, which is a division of application No. 09/115,446, filed on Jul. 14, 1998, now Pat. No. 6,165,719.

(60) Provisional application No. 60/070,741, filed on Jan. 8, 1998, provisional application No. 60/052,556, filed on Jul. 15, 1997.

(51) Int. Cl.
C07K 14/705 (2006.01)
(52) U.S. Cl. .......................................... 530/350; 514/2
(58) Field of Classification Search ...................... None
See application file for complete search history.

(56) References Cited

U.S. PATENT DOCUMENTS 5,637,470 A * 6/1997 Kaczorowski et al. ...... 435/7.21
5,776,734 A * 7/1998 Kaczorowski et al. ...... 435/69.1

FOREIGN PATENT DOCUMENTS

WO WO 98/11139 * 3/1998 ................ 435/69.1

OTHER PUBLICATIONS

Bowie et al. (1989) Science 247: 1306-1310.*
Imbert et al., Cloning of the gene for the spinocerebellar, *Nature Genetics*, vol. 14, pp. 258-291, Nov. 1996.*
Imbert et al., "Cloning of the gene for spinocerebellar ataxia 2 reveals a locus with high sensitivity to expanded CAG/glutamine repeats", Nature Genetics, vol. 14, pp. 285-291, Nov. 1996.*
Stratagene catalog, p. 39, 1988.*
Imbert et al., "Cloning of the gene for spinocerebellar ataxia 2 reveals a locus with high sensitivity to expanded CAG/glutamine repeats", *Nature Genetics*, (1996), vol. 14, pp. 285-291.*

Imbert et al., "Cloning of the Gene for Spinocerebellar Ataxia 2 Reveals a Locus with High Sensitivity to Expanded CAG/Glutamine Repeats," Nature Genetics, vol. 14, No. 3, pp. 285-291, Nov. 1996.
M. Kohler, "Small-Conductance, Calcium-Activated Potassium Channels from Mammalian Brain," Science, vol. 273, pp. 1625-1764, Sep. 1996.
William J. Joiner, "hSK4, A Member of a Novel Subfamily of Calcium-Activated Potassium Channels," Neurobiology, vol. 94, pp. 11013-11018, Sep. 1997.
Takahiro M. Ishii, "A Human Intermediate Conductance Calcium-Activated Potassium Channel," Neurobiology, vol. 94, pp. 11651-11656, Oct. 1997.
Gilliam P. Bates, "Transgenic Mouse Models of Neurodegenerative disease Cause by CAG/Polyglutamine Expansions," Molecular Medicine Today, Nov. 1997.
P.S. Reddy et al., "The Complex Pathology of Trinucleotide Repeats" Current Opinion Cell Biology, vol. 9, No. 3, pp. 364-372, Jun. 1997.
Georges Imbert, Cloning of the gene for spinocerebellar ataxia 2 reveals a locus with high sensitivity to expanded CAG/glutamine repeats, Nov. 1996, Nature Genetics vol. 14 No. 3. , pp. 285-291.
M. Kohler, Small-Conductance, Calcium-Activated Potassium Channels from Mammalian Brain, Sep. 1996, Science, vol. 273 pp. 1625-1764.

(Continued)

*Primary Examiner*—Michael Pak
(74) *Attorney, Agent, or Firm*—DLA Piper US LLP

(57) ABSTRACT

The present invention is based on the discovery and cloning of the human small conductance calcium activated potassium channel type 3 (hKCa3/KCNN3) gene, which is expressed in neuronal cells, skeletal muscle, heart, and lymphocytes. Alterations in the hKCa3/KCNN3 gene or its protein product may enhance susceptibility to schizophrenia and/or bipolar disorder. hKCa3/KCNN3 may be involved in neuropsychiatric, neurological, neuromuscular, and immunological disorders. Substantially purified hKCa3/KCNN3 polypeptides and polynucleotides are provided. Antibodies which bind to hKCa3/KCNN3 polypeptides are also disclosed. A method for identifying a compound which affects hKCa3/KCNN3 polynucleotide or polypeptide is provided. A method for diagnosis and determining the prognosis and treatment regimen of a subject having or at risk of having a hKCa3/KCNN3-associated disorder is also provided. A method of treating a subject having or at risk of having an hKCa3/KCNN3-associated disorder by administering a therapeutically effective amount of a polynucleotide encoding SEQ ID NO:2 is also provided. A formulation for administration of hKCa3/KCNN3 to a patient of a therapeutically effective amount of hKCa3/KCNN3 polypeptide is provided. Kits useful for detecting the presence of hKCa3/KCNN3 polypeptide or polynucleotide in a sample from a subject having a hKCa3/KCNN3-associated disorder are provided. Transgenic nonhuman animals having a transgene encoding hKCa3/KCNN3 are also described.

5 Claims, 15 Drawing Sheets

OTHER PUBLICATIONS

William J. Joiner, hSK4, a member of a novel subfamily of calcium-activated potassium channels, Sep. 1997, Neurobiology, vol. 94 pp. 11013-11018.

Takahiro M. Ishii, A human intermediate conductance calcium-activated potassium channel, Oct. 1997, Neurobiology, vol. 94 pp. 11651-11656.

Gillian P. Bates, Tansgenic mouse models of neurodegenerative disease caused by CAG/polyglutamine expansions, Nov. 1997, Molecular Medicine Today.

P Sanjeeva Reddy, The complex pathology of trinucleotide repeats, Nucleus and gene expression, pp. 364-372.

T Bowen, Further support for an association between a polymorphic CAG repeat in the hKCa3 gene and schizophrenia, 1998, Molecular Psychiatry.

Kohler et al., Small Conductance, Calcium-Activated Potassium Channels from Mammalian Brain. Science. Sep. 20, 1996, vol. 273, pp. 1709-1714, expecially figures 1A and 1C on p. 1710.

* cited by examiner

FIGURE 1A

```
hskca3d seq  (Our sequence)
Y08263 SEQ   (AAD14 sequence)
G16005 SEQ   (Genomic sequence in STS database)
U69884 SEQ   rat SKCa3 (old sequence)
R69884 SEQ   rat SKCa3 (revised October 1997)

hSkca3   GCCTCACACGCTCCTAGAGGACCACCTCCTGAGAGAGTTCTTTCACCCCCTCTTCTTTCTCCAAGCTCCC     70
AAD14    ----------------------------------------------------------------------     70 hSkca3   CTCCTGCTCTCCCTCCCTGCCCAATACAATGCATTCTTGAGTGGCAGCGTCTGGACTCCAGGCAGCCCA     140
AAD14    ----------------------------------------------------------------------    140 hSkca3   GAGAACCGAAGCAAGCCAAAGAGAGGACTGGAGCCAAGATACTGGTGGGGGAGATTGCATGCCTGGCTTT    210
AAD14    ----------------------------------------------------------------------    210 hSkca3   CTTTGAGGACATCTTTGGAGCGAGGGTGGCTTTGGGGTGGGGGCTTGTGCTGCAGGGAATACAGCCAGGC    280
AAD14    ----------------------------------------------------------------------    280 hSkca3   CCCAAGATGGACACTTCTGGGCACTTCCATGACTCGGGGGTGGGGGACTTGGATGAAGACCCCAAGTGCC    350
AAD14    ----------------------------------------------------------------------    350
G16005                                          ---------------N---------     23
R69884   C---------------------G--------------TC---------------------T-         65

╔═══════Trinucleotide repeat═══════╗
hSkca3   CCTGTCCATCCTCTGGGGATGAGCAGCAGCAGCAGCAGCAGCAGCAACAGCAGCAGCCACCACCGCC     420
AAD14    -----------------------------------------------------------------T-    420
G16005   -N-N-------------------------------------------------------------      93
R69884   -----------T---------C-----A---------A-----A-C--C--CA-  -GT---- G-----AG-  135

┌──
hSkca3   AGCGTCACC AGCAGCCCCCCAGCAGCCCCTGGGACCCTCGCTGCAGCCTCAGCCTCCGCAGCTTCAGCA   490
AAD14    --T------ --T--T-------------------------------------------------------   490
G16005   ----C----                                 --T--------------------N----   163
R69884   --  --C--C--------    T-C--------T--------------------------            205

╔════Trinucleotide repeat════════════╗
hSkca3   GCAGCAGCAGCAGCAGCAGCAGCAGCAGCAGCAG              TCACCGCATCCCCTG        560
AAD14    ---------------------------------              ---------------        560
G16005   ---------------------------------CAGCAGCAGCAGCAGTCNNNN-ANNNNNNNNNN     233
R69884   ---------------------------------CAGCAGCAGCAGCAGGCTC----T---C------   275 hSkca3   TCTCAGCTCGCCCAACTCCAGAGCCAGCCCGTCCACCCTGGCCTGCTGCACTCCTCTCCCA  CCGCTTT   630
AAD14    ------T---------------T------------------------------------  -------   630
G16005   NNNNNNNNNNNNNNNNNNNNNNN                        --N----------A-AN------  303
R69884   C--------T-------------------GTT-----T-----T---T--------T--------  -G-----  345
```

FIGURE 1B

```
         | *     |         |         |         |         |         |
hSkca3   CAGGGCCCCCCC TTCGTCCAACTCCACCGCCATCCTCCACCCTTCCTCC AGGCAAGGCAGCCAGCTCA    700
AAD14    -------------C-----------------T---------------------- ----------------------    700
G16005   A-------NN--NC----------------------A-NN--------C-----------------------    373
R69884   ------T---AAT- -AG----------------------------------- ------------------A-    415

**| *     |         |         |         |         |         |
hSkca3   ATCTCAATGACCACTTGCTTGGCCACTCTCCAAGTTCCACAGCTACAAGTGGGCCTGGCGGAGGCAGCCG      770
AAD14    ------------------------------------------T-----------------T------    770
G16005   ---------------------------------------------------------------------    443
R69884   ---------------G-------------------------C------------T-----------    485

|         |         |         |         |         |         |
hSkca3   GCACCGACAGGCCAGCCCCCTGGTGCACCGGCGGGACAGCAACCCCTTCACGGAGATCGCCATGAGCTCC      840
AAD14    ----------------------------------------------------------------------      840
G16005   ----------------------------------------------------------------------      513
U69884                                                            -------             9
R69884   ------G-----------G-----------------T--------------A--T-----------      555

|         |         |         |         |         |         |
hSkca3   TGCAAGTATAGCGGTGGGGTCATGAAGCCCCTCAGCCGCCTCAGCGCCTCCCGGAGGAACCTCATCGAGG      910
AAD14    --------------------------------T-------------------------------------      910
G16005   ----------------------------------------------------------------------      583
U69884   -----A--C------------------------------------T-----A-----T-------       79
R69884   -----A--C------------------A---------------T----A-----T------       625

|         |         |         |         |         |         |
hSkca3   CCGAGACTGAGGGCCAACCCCTCCAGCTTTTCAGCCCTAGCAACCCCCCGGAGATCGTCATCTCCTCCCG      980
AAD14    ----------------------------------------------------------------------      980
G16005   ----------------------------------------------------                      653
U69884   -----C-------------------C-----T--C----------A-----TA------------A-      149
R69884   -----C-------------------C-----T--C----------A-----TA------------A-      695

|         |         |         |         |         |         |
hSkca3   GGAGGACAACCATGCCCACCAGACCCTGCTCCATCACCCTAATGCCACCCACAACCACCAGCATGCCGGC    1,050
AAD14    ----------------------------------------------------------------------    1,050
U69884   ------T------------------T-----------C--C--T-------------------      219
R69884   ------T------------------T-----------C--C--T-------------------      765

|         |         |         |         |         |         |
hSkca3   ACCACCGCCAGCAGCACCACCTTCCCCAAAGCCAACAAGCGGAAAAACCAAAACATTGGCTATAAGCTGG    1,120
AAD14    ----------------------------------------------------------------------    1,120
U69884   -----T--TG---------------------------------------------------      289
R69884   -----T--TG---------------------------------------------------      835

|         |         |         |         |         |         |
hSkca3   GACACAGGAGGGCCCTGTTTGAAAAGAGAAAGCGACTGAGTGACTATGCTCTGATTTTTCGGATGTTTGG    1,190
AAD14    ----------------------------------------------------------------------    1,190
U69884   -G-------------------------------------------------------------      359
R69884   -G-------------------------------------------------------------      905

|         |         |         |         |         |         |
hSkca3   AATTGTTGTTATGGTGATAGAGACCGAGCTCTCTTGGGGTTTGTACTCAAAGGACTCCATGTTTTCGTTG    1,260
AAD14    ----------------------------------------------------------------------    1,260
U69884   -------------------A--G-------------------T--------------      429
R69884   -------------------A--G-------------------T--------------      975
```

FIGURE 1C

```
hSkca3  GCCCTGAAATGCCGTATCAGTCTGTCCACCATCATCCTTTTGGGCTTGATCATCGCCTACCACACACGTG  1,330
AAD14   ------------------------------------------------------------------  1,330
U69884  -----------T-------T-A--------------GC-T--T-------------------A-G-  499
R69884  -----------T-------T-A--------------GC-T--T-------------------A-G-  1,045 hSkca3  GAGTCCAGCTCTTCGTGATCGACAACGACGCGGATGACTGGCGGATAGCCATGACCTACGAGCGCATCCT  1,400
AAD14   ------------------------------------------------------------------  1,400
U69884  A---A--------T-----------T-GT--A-----------------------T----------  569
R69884  A---A--------T-----------T-GT--A-----------------------T----------  1,115 hSkca3  CTACATTAGCCTGGAGATGCTGGTGTACACAAACCACACCATTCCTGGCGAGTACAAGTTCTTCTGGGCG  1,470
AAD14   ------------------------------------------------------------------  1,470
U69884  ------C----------------G-G-C-T----C-----------A-----------------A--  639
R69884  ------C----------------G-G-C-T----C-----------A-----------------A--  1,185 hSkca3  GCACGCCTGGCCTTCTCCTACACACCCTCCCGGGCGGAGGCCGATGTGGACATCATCCTGTCTATCCCCA  1,540
AAD14   ------------------------------------------------------------------  1,540
U69884  -------------------C-----T-----A-----T--C---------T--T-----C-------  709
R69884  -------------------C-----T-----A-----T--C---------T--T-----C-------  1,255 hSkca3  TGTTCCTGCGCCTGTACCTGATCGCCCGAGTCATGCTGCTACACAGCAAGCTCTTCACCGATGCCTCGTC  1,610
AAD14   ------------------------------------------------------------------  1,610
U69884  -----T-------A--------------------------T------------G-------A--  779
R69884  -----T-------A--------------------------T------------G-------A--  1,325 hSkca3  CCGCAGCATCGGGGCCCTCAACAAGATCAACTTCAACACCCGCTTT GTCAT GAAGACGCTCATGACCA  1,680
AAD14   ------------------------------------T-----T---------------------  1,680
U69884  ---A-----------------------------------A-C- -----  -----------------  849
R69884  ---A-----------------------------------A-C- -----  -----------------  1,395 hSkca3  TCTGCCCTGGCACTGTGCTGCTCGTGTTCAGCATCTCTCTGTGGATCATTGCTGCCTGGACCGTCCGTGT  1,750
AAD14   ------------------------------------------------------------------  1,750
U69884  -------G-----G--------AA-------------------C-----------T--GA-A--  919
R69884  -------G-----G--------G--------------------C-----------T--GA-A--  1,465 hSkca3  CTGTGAAAGGTACCATGACCAGCAGGACGTAACTAGTAACTTTCTGGGTGCCATGTGGCTCATCTCCATC  1,820
AAD14   ------------------------------------------------------------------  1,820
U69884  ------------------------------------------------------------------  989
R69884  ------------------------------------------------------------------  1,535 hSkca3  ACATTCCTTTCCATTGGTTATGGGGACATGGTGCCCCACACATACTGTGGGAAAGGTGTCTGTCTCCTCA  1,890
AAD14   ------------------------------------------------------------------  1,890
U69884  --G----------C-----------------------------------------T----  1,059
R69884  --G----------C-----------------------------------------T----  1,605 hSkca3  CTGGCATCATGGGTGCAGGCTGCACTGCCCTTGTGGTGGCCGTGGTGGCCCGAAAGCTGGAACTCACCAA  1,960
AAD14   ------------------------------------------------------------------  1,960
U69884  ------------------------C-----A--T-----T-----G-----C------------  1,129
R69884  ------------------------C-----A--T-----T-----G-----C------------  1,675
```

FIGURE 1D

```
            |         |         |         |         |         |         |
hSkca3  AGCGGAGAAGCACGTGCATAACTTCATGATGGACACTCAGCTCACCAAGCGGATCAAGAATGCTGCAGCA  2,030
AAD14   ---------------CG-                                                     2,030
U69884  ---A--------T-----C-----------------------------A-----------C-----C--C  1,199
R69884  ---A--------T-----C-----------------------------A-----------C-----C--C  1,745

|         |         |         |         |         |         |
hSkca3  AATGTCCTTCGGGAAACATGGTTAATCTATAAACACACAAAGCTGCTAAAGAAGATTGACCATGCCAAAG  2,100
U69884  --------C-----------C-G-----C-----------------------------------C------  1,269
R69884  --------C-----------C-G-----C-----------------------------------C------  1,815

|         |         |         |         |         |         |
hSkca3  TGAGGAAACACCAGAGGAAGTTCCTCCAAGCTATCCACCAGTTGAGGAGCGTCAAGATGGAACAGAGGAA  2,170
U69884  -C-------------------------------------T-----AC-----G-T--------------A-----  1,339
R69884  -C-------------------------------------T-----AC-----G-T--------------A-----  1,885

|         |         |         |         |         |         |
hSkca3  GCTGAGTGACCAAGCCAACACTCTGGTGGACCTTTCCAAGATGCAGAATGTCATGTATGACTTAATCACA  2,240
U69884  ----------------------C----------------------------C---------------G-----G  1,409
R69884  ----------------------C----------------------------C---------------G-----G  1,955

|         |         |         |         |         |         |
hSkca3  GAACTCAATGACCGGAGCGAAGACCTGGAGAAGCAGATTGGCAGCCTGGAGTCGAAGCTGGAGCATCTCA  2,310
U69884  --G-----C--------T----------A-----------------------A--C-----------C----  1,479
R69884  --G-----C--------T----------A-----------------------A--C-----------C----  2,025

|         |         |         |         |         |         |
hSkca3  CCGCCAGCTTCAACTCCCTGCCGCTGCTCATCGCCGACACCCTGCGCCCAGCAGCAGCAGCAGCTCCTGTC  2,380
U69884  -A-----------T--------C----------A-----------A----------------G--CA-  1,549
R69884  -A-----------T--------C----------A-----------A----------------G--CA-  2,095

|         |         |         |         |         |         |
hSkca3  TGCCATCATCGAGGCCCGGGGTGTCAGCGTGGCAGTGGGCACCACCCACACCCCAATCTCCGATACGCCC  2,450
U69884  ----T--G-G-----------CA----T-----T-----A--T-G----G-----TCC---T--C-GC--T  1,619
R69884  ----T--G-G-----------CA----T-----T-----A--T-G----G-----TCC---T--C-GC--T  2,165

|         |         |         |         |         |         |
hSkca3  ATTGGGGTCAGCTCCACCTCCTTCCCGACCCCGTACACAAGTTCAAGCAGTTGCTAAATAAATCTCCCCA  2,520
U69884  --C---A-------------T------GAATTCCTA-T-TTC-AG                           1,689
R69884  --C---A-------------T-----A-----A-----------------------A--------       2,235

|         |
hSkca3  CTCCAGAAGCATTAAAAAAAAAAAA     2,590
R69884  ------------                  2,305
```

FIGURE 2A hskca3.pep (our sequence)
u69884.pep (old rat sequence)
r69884.pep (rat sequence revised in October 1997)
y08263.pep (AAD14 frame 1)
yC82631.pep (AAD14 frame 2)
yC82632.pep (AAD14 frame 3)

```
                                             ┌─Poly Q rpt─┐
                  |         |         |      |    |        |       |
hSKCa3    MDTSGHFHDSGVGDLDEDPKCPCPSSGDEQQQQQQQQQQQQPPPP ASPAAPQQPLGPSLQPQPPQLQQQ    70
R69884    -------.--E-------------------------------- ----S-P--V----P--L---------   70
AAD14 F1  ------------------------------------------- SV---VV-------------------   70

Poly Q rpt
                  |             |         |         |         |         |         |
hSKCa3    QQQQQQQQQQQS    PHPLSQLAQLQSQPVHPGLLHSSPTAFRAPPSSNSTAILHPSSRQGSQLNLN   140
R69884    ------------QQQQQAPL---P--------V-----------N-A-------------------   140
AAD14 F1  ------------    ------F------S-------------FVQLHRHPP-FLQARQPAQSQ   140

|         |         |         |         |         |         |
hSKCa3    DHLLGHSPSSTATSGPGGGSRHRQASPLVHRRDSNPFTEIAMSSCKYSGGVMKPLSRFSASRRNLIEAET   210
R69884    ---V-----------------V------------------------N-L-----------P       210
AAD14 F2  ------------------------------------------------------------         29

|         |         |         |         |         |         |
hSKCa3    EGQPLQLFSPSNPPEIVISSREDNHAHQTLLHHPNATHNHQHAGTTASSTTFPKANKRKNQNIGYKLGHR   280
U69884    ----------------I-------------------------G----------------------    99
R69884    ----------------I-------------------------G----------------------   280
AAD14 F2  -----------------------------------------------------------------    99

┌═════S1═════┐              ┌═════S2══════┐
                  |         |         |         |         |         |         |
hSKCa3    RALFEKRKRLSDYALIFGMFGIVVMVIETELSWGLYSKDSMFSLALKCRISLSTIILLGLIIAYHTRGVQ   350
U69884    --------------------------------------L---------------------E--   169
R69884    --------------------------------------L---------------------E--   350
AAD14 F2  ----------------------------------------------------------------   169

┌══════S3═══════┐              ┌───S4───
                  |         |         |         |         |         |         |
hSKCa3    LFVIDNDADDWRIAMTYERILYISLEMLVYTNHTIPGEYKFFWAARLAFSYTPSRAEADVDIILSIPMFL   420
U69884    ------G-----------------CAI-P-------T---------------------------   239
R69884    ------G-----------------CAI-P-------T---------------------------   420
AAD14 F2  ----------------------------------------------------------------   239

══S4══┐                              ┌═════S5══════
                  |         |         |         |         |         |         |
hSKCa3    RLYLIARVMLLHSKLFTDASSRSIGALNKINFNTRFVMKTLMTICPGTVLLVFSISLWIIAAWTVRVCER   490
U59884    ----------------------------------------M-----------------------   309
R69884    ----------------------------------------------------------------   490
AAD14 F2  ----------------------CH                                             309

┌══════P-reg══════┐              ┌═════S6══════┐
                  |         |         |         |         |         |         |
hSKCa3    YHDQQDVTSNFLGAMWLISITFLSIGYGDMVPHTYCGKGVCLLTGIMGAGCTALVVAVVARKLELTKAEK   560
U69884    ----------------------------------------------------------------   379
R69884    ----------------------------------------------------------------   560
AAD14 F3  ----------------------------------------------------------------   102
```

FIGURE 2B

```
        |         |         |         |         |         |         |
hSKCa3  HVDNFMMDTQLTKRIKNAAANVLRETWLIYKHTKLLKKIDHAKVRKHQRKFLQAIHQLRSVKMEQRKLSD    630
U69884  --H---------------------------------------------------G-----------    449
R69884  --H---------------------------------------------------G-----------    630
AAD14 F3 --                                                                  172

|         |         |         |         |         |         |
hSKCa3  QANTLVDLSKMQNVMYDLITELNDRSEDLEKQIGSLESKLEHLTASFNSLPLLIADTLRQQQQQLLSAII    700
U69884  ----------------------------------------------------------------T-FV    519
R69884  ----------------------------------------------------------------T-FV    700

|         |         |         |
hSKCa3  EARGVSVAVGTTHTPISDTPIGVSSTSFPTPYTSSSSC        770
U69884  ----I------S-A-P--S---I------EFLIF            589
R69884  ----I------S-A-P--S---I---------              770
```

FIGURE 5A

NUCLEOTIDE SEQUENCE AND TRANSLATION OF hKCa3

```
     -286        -280         -270         -260          -250         -240
            GCCTCA  CACGCTCCTA  GAGGACCACC  TCCTGAGAGA  GTTCTTTCAC  CCCCTCTTCT

-230        -220         -210         -200          -190         -180
         TTCTCCAAGC  TCCCCTCCTG  CTCTCCCTCC  CTGCCCAATA  CAATGCATTC  TTGAGTGGCA

-170        -160         -150         -140          -130         -120
         GCGTCTGGAC  TCCAGGCAGC  CCCAGAGAAC  CGAAGCAAGC  CAAAGAGAGG  ACTGGAGCCA

-110        -100          -90          -80           -70          -60
         AGATACTGGT  GGGGGAGATT  GGATGCCTGG  CTTTCTTTGA  GGACATCTTT  GGAGCGAGGG

-50         -40          -30          -20           -10
         TGGCTTTGGG  GTGGGGGCTT  GTGCTGCAGG  GAATACAGCC  AGGCCCCAAG  ATG GAC ACT
                                                                     Met Asp Thr 15                      30                      45                      60
         TCT GGG CAC TTC CAT GAC TCG GGG GTG GGG GAC TTG GAT GAA GAC CCC AAG TGC
         Ser Gly His Phe His Asp Ser Gly Val Gly Asp Leu Asp Glu Asp Pro Lys Cys 75                      90                     105
         CCC TGT CCA TCC TCT GGG GAT GAG CAG CAG CAG CAG CAG CAG CAG CAA CAG CAG
         Pro Cys Pro Ser Ser Gly Asp Glu Gln Gln Gln Gln Gln Gln Gln Gln Gln Gln 120                    135                     150                    165
         CAG CAG CCA CCA CCG CCA GCG CCA CCA GCA GCC CCC CAG CAG CCC CTG GGA CCC
         Gln Gln Pro Pro Pro Pro Ala Pro Pro Ala Ala Pro Gln Gln Pro Leu Gly Pro 180                     195                    210                    225
         TCG CTG CAG CCT CAG CCT CCG CAG CTT CAG CAG CAG CAG CAG CAG CAG CAG CAG
         Ser Leu Gln Pro Gln Pro Pro Gln Leu Gln Gln Gln Gln Gln Gln Gln Gln Gln 240                     255                    270
         CAG CAG CAG CAG CAG CCA CCC CAT CCC CTG TCT CAG CTC GCC CAA CTC CAG AGC
         Gln Gln Gln Gln Gln Pro Pro His Pro Leu Ser Gln Leu Ala Gln Leu Gln Ser 285                     300                    315                    330
         CAG CCC GTC CAC CCT GGC CTG CTG CAC TCC TCT CCC ACC GCT TTC AGG GCC CCC
         Gln Pro Val His Pro Gly Leu Leu His Ser Ser Pro Thr Ala Phe Arg Ala Pro 345                     360                    375
         CCT TCG TCC AAC TCC ACC GCC ATC CTC CAC CCT TCC TCC AGG CAA GGC AGC CAG
         Pro Ser Ser Asn Ser Thr Ala Ile Leu His Pro Ser Ser Arg Gln Gly Ser Gln 390                    405                     420                    435
         CTC AAT CTC AAT GAC CAC TTG CTT GGC CAC TCT CCA AGT TCC ACA GCT ACA AGT
         Leu Asn Leu Asn Asp His Leu Leu Gly His Ser Pro Ser Ser Thr Ala Thr Ser 450                     465                    480                    495
         GGG CCT GGC GGA GGC AGC CGG CAC CGA CAG GCC AGC CCC CTG GTG CAC CGG CGG
         Gly Pro Gly Gly Gly Ser Arg His Arg Gln Ala Ser Pro Leu Val His Arg Arg
```

FIGURE 5B

```
            510                      525                      540
GAC AGC AAC CCC TTC ACG GAG ATC GCC ATG AGC TCC TGC AAG TAT AGC GGT GGG
Asp Ser Asn Pro Phe Thr Glu Ile Ala Met Ser Ser Cys Lys Tyr Ser Gly Gly 555                      570                      585                      600
GTC ATG AAG CCC CTC AGC CGC CTC AGC GCC TCC CGG AGG AAC CTC ATC GAG GCC
Val Met Lys Pro Leu Ser Arg Leu Ser Ala Ser Arg Arg Asn Leu Ile Glu Ala 615                      630                      645
GAG ACT GAG GGC CAA CCC CTC CAG CTT TTC AGC CCT AGC AAC CCC CCG GAG ATC
Glu Thr Glu Gly Gln Pro Leu Gln Leu Phe Ser Pro Ser Asn Pro Pro Glu Ile 660                      675                      690                      705
GTC ATC TCC TCC CGG GAG GAC AAC CAT GCC CAC CAG ACC CTG CTC CAT CAC CCT
Val Ile Ser Ser Arg Glu Asp Asn His Ala His Gln Thr Leu Leu His His Pro 720                      735                      750                      765
AAT GCC ACC CAC AAC CAC CAG CAT GCC GGC ACC GCC GCC AGC AGC ACC ACC TTC
Asn Ala Thr His Asn His Gln His Ala Gly Thr Ala Ala Ser Ser Thr Thr Phe 780                      795                      810
CCC AAA GCC AAC AAG CGG AAA AAC CAG AAC ATT GGC TAT AAG CTG GGA CAC AGG
Pro Lys Ala Asn Lys Arg Lys Asn Gln Asn Ile Gly Tyr Lys Leu Gly His Arg 825                      840                      855                      870
AGG GCC CCG TTT GAA AAG AGA AAG CGA CTG AGT GAC TAT GCT CTG ATT TTT GGG
Arg Ala Pro Phe Glu Lys Arg Lys Arg Leu Ser Asp Tyr Ala Leu Ile Phe Gly 885                      900                      915
ATG TTT GGA ATT GTT GTT ATG GTG ATA GAG ACC GAG CTC TCT TGG GGT TTG TAC
Met Phe Gly Ile Val Val Met Val Ile Glu Thr Glu Leu Ser Trp Gly Leu Tyr 930                      945                      960                      975
TCA AAG GAC TCC ATG TTT TCG TTG GCC CTG AAA TGC CTT ATC AGT CTG TCC ACC
Ser Lys Asp Ser Met Phe Ser Leu Ala Leu Lys Cys Leu Ile Ser Leu Ser Thr 990                      1005                     1020                     1035
ATC ATC CTT TTG GGC TTG ATC ATC GCC TAC CAC ACA CGT GAA GCC CAG CTC TTC
Ile Ile Leu Leu Gly Leu Ile Ile Ala Tyr His Thr Arg Glu Ala Gln Leu Phe 1050                     1065                     1080
GTG ATC GAC AAT GGC GCG GAT GAC TGG CGG ATA GCC ATG ACC TAC GAG CGC ATC
Val Ile Asp Asn Gly Ala Asp Asp Trp Arg Ile Ala Met Thr Tyr Glu Arg Ile 1095                     1110                     1125                     1140
CTG TAC ATC AGC CTG GAG ATG CTG GTG TGC GCC ATC CAC CCC ATT CCT GGC GAG
Leu Tyr Ile Ser Leu Glu Met Leu Val Cys Ala Ile His Pro Ile Pro Gly Glu 1155                     1170                     1185
TAC AAG TTC TTC TGG ACG GCT CGC CTG GCC TTC TCC TAC ACA CCC TCC CGG GCG
Tyr Lys Phe Phe Trp Thr Ala Arg Leu Ala Phe Ser Tyr Thr Pro Ser Arg Ala
```

FIGURE 5C

```
1200                1215                1230                1245
GAG GCC GAT GTG GAC ATC ATC CTG TCT ATC CCC ATG TTC CTG CGC CTG TAC CTG
Glu Ala Asp Val Asp Ile Ile Leu Ser Ile Pro Met Phe Leu Arg Leu Tyr Leu 1260                1275                1290                1305
ATC GCC CGA GTC ATG CTG CTG CAC AGC AAG CTC TTC ACC GAT GCC TCG TCC CGC
Ile Ala Arg Val Met Leu Leu His Ser Lys Leu Phe Thr Asp Ala Ser Ser Arg 1320                1335                1350
AGC ATC GGG GCC CTC AAC AAG ATC AAC TTC AAC ACC CGC TTT GTC ATG AAG ACG
Ser Ile Gly Ala Leu Asn Lys Ile Asn Phe Asn Thr Arg Phe Val Met Lys Thr 1365                1380                1395                1410
CTC ATG ACC ATC TGC CCT GGC ACT GTG CTC CTG GTG TTC AGC ATC TCT CTG TGG
Leu Met Thr Ile Cys Pro Gly Thr Val Leu Leu Val Phe Ser Ile Ser Leu Trp 1425                1440                1455
ATC ATT GCT GCC TGG ACC GTC CGT GCC TGT GAA AGG TAC CAT GAC CAG CAG GAC
Ile Ile Ala Ala Trp Thr Val Arg Ala Cys Glu Arg Tyr His Asp Gln Gln Asp 1470                1485                1500                1515
GTA ACT AGT AAC TTT CTG GGT GCC ATG TGG CTC ATC TCC ATC ACA TTC CTT TCC
Val Thr Ser Asn Phe Leu Gly Ala Met Trp Leu Ile Ser Ile Thr Phe Leu Ser 1530                1545                1560                1575
ATT GGT TAT GGG GAC ATG GTG CCC CAC ACA TAC TGT GGG AAA GGT GTC TGT CTC
Ile Gly Tyr Gly Asp Met Val Pro His Thr Tyr Cys Gly Lys Gly Val Cys Leu 1590                1605                1620
CTC ACT GGC ATC ATG GGT GCA GGC TGC ACT GCC CTT GTG GTG GCC GTG GTG GCC
Leu Thr Gly Ile Met Gly Ala Gly Cys Thr Ala Leu Val Val Ala Val Val Ala 1635                1650                1665                1680
CGA AAG CTG GAA CTC ACC AAA GCG GAG AAG CAC GTT CAT AAC TTC ATG ATG GAC
Arg Lys Leu Glu Leu Thr Lys Ala Glu Lys His Val His Asn Phe Met Met Asp 1695                1710                1725
ACT CAG CTC ACC AAG CGG ATC AAG AAT GCT GCA GCC AAT GTC CTT CGG GAA ACA
Thr Gln Leu Thr Lys Arg Ile Lys Asn Ala Ala Ala Asn Val Leu Arg Glu Thr 1740                1755                1770                1785
TGG TTA ATC TAT AAA CAC ACA AAG CTG CTA AAG AAG ATT GAC CAT GCC AAA GTG
Trp Leu Ile Tyr Lys His Thr Lys Leu Leu Lys Lys Ile Asp His Ala Lys Val 1800                1815                1830                1845
AGG AAA CAC CAG AGG AAG TTC CTC CAA GCT ATC CAC CAG TTG AGG AGC GTC AAG
Arg Lys His Gln Arg Lys Phe Leu Gln Ala Ile His Gln Leu Arg Ser Val Lys 1860                1875                1890
ATG GAA CAG AGG AAG CTG AGT GAC CAA GCC AAC ACT CTG GTG GAC CTT TCC AAG
Met Glu Gln Arg Lys Leu Ser Asp Gln Ala Asn Thr Leu Val Asp Leu Ser Lys
```

FIGURE 5D

```
         1905                   1920                   1935                   1950
ATG CAG AAT GTC ATG TAT GAC TTA ATC ACA GAA CTC AAT GAC CGG AGC GAA GAC
Met Gln Asn Val Met Tyr Asp Leu Ile Thr Glu Leu Asn Asp Arg Ser Glu Asp 1965                   1980                   1995
CTG GAG AAG CAG ATT GGC AGC CTG GAG TCG AAG CTG GAG CAT CTC ACC GCC AGC
Leu Glu Lys Gln Ile Gly Ser Leu Glu Ser Lys Leu Glu His Leu Thr Ala Ser 2010                   2025                   2040                   2055
TTC AAC TCC CTG CCG CTG CTC ATC GCC GAC ACC CTG CGC CAG CAG CAG CAG CAG
Phe Asn Ser Leu Pro Leu Leu Ile Ala Asp Thr Leu Arg Gln Gln Gln Gln Gln 2070                   2085                   2100                   2115
CTC CTG TCT GCC ATC ATC GAG GCC CGG GGT GTC AGC GTG GCA GTG GGC ACC ACC
Leu Leu Ser Ala Ile Ile Glu Ala Arg Gly Val Ser Val Ala Val Gly Thr Thr 2130                   2145                   2160
CAC ACC CCA ATC TCC GAT AGC CCC ATT GGG GTC AGC TCC ACC TCC TTC CCG ACC
His Thr Pro Ile Ser Asp Ser Pro Ile Gly Val Ser Ser Thr Ser Phe Pro Thr 2175                   2190                   2205                   2220
CCG TAC ACA AGT TCA AGC AGT TGC TAA ATA AAT CTC CCC ACT CCA GAA GCA TTA
Pro Tyr Thr Ser Ser Ser Ser Cys  *

2235
AAA AAA AAA AAA
```

FIGURE 6

Alignment of cDNA and Genomic sequence of hKCa3
showing intron/exon boundary

```
                1140      1150      1160      1170      1180      1190
hKCa3f.seq   ACTGAGTGACTATGCTCTGATTTTTGGGATGTTTGGAATTGTTGTTATGGTGATAGAGA
             ||||||||||||||||||||||||||||||||||||||||||||||||||||||||||
B1-1395.SEQ  ACTGAGTGACTATGCTCTGATTTTTGGGATGTTTGGAATTGTTGTTATGGTGATAGAGA 1200      1210      1220      1230      1240      1250
hKCa32f.seq  CCGAGCTCTCTTGGGGTTTGTACTCAAAGGACTCCATGTTTTCGTTGGCCCTGAAATGCC
             ||||||||||||||||||||||||||||||||||
B1-1395.SEQ  CCGAGCTCTCTTGGGGTTTGTACTCAAAGGTAGGGGCTGTGGTTTCTCTTTATACCTTGA
                                           ↑ begin Intron 1

B1-1395.SEQ  ACAAAAGGAATATGTAGGTAGCAAGAGAGGGATTGAGAGAGGGGATATTGAGAGAGAGA

B1-1395.SEQ  GAGAGAGAGAGAGAGAGAGATTGAGAGATTGGGAGGGAGACTGGGAGAGAGAGGTGGTGG

B1-1395.SEQ  TGGTGGTGAGAGGCGCTTGCTCAGTTATAT
```

Genomic map of hKCa3, first exon

FIGURE 8

5' Flanking/Untranslated sequence of hKCa3/KCNN3

```
CCC TTG AAC ACG AGG CGT TAG ACA CTC CAG TCC ATG    36
GTA GGT TAG TTT TTA TCC NCC GGG GTG TTA GAA ACG    72
TGG GNA TCC CCC CCT GGT TCT GTG ACC TTT GAC GTT   108
GTT ACT CAA CAC CTT TTA AGC ATC AGG CTT TGT AAA   144
TTG AGA CCA TAC TGG CCC ACC TCC TTG GGT GTT TGA   180
AGA CTG TAT CCG GAT AAT ATA TGT GAA ACN ACC TAT   216
CGT AAA CCC TGG TGG TTA ATA AAT GTT TGC CTT CCC   252
CTC CGT CTG CCC CCT TCA TCC AGG GTG CAC ACC TCC   288
CCT CCT TCG GAG GCC CTC TGT CCC TCC TCC CCA TCG   324
CCC AGC GTG AGC GAA CAT CCC TTA TCG CCG TGG GCT   360
TAA GGG TTG TGG CCA TAC CTG TCA GAG GAA AGA GGA   396
CAG CGG CTC AGC TCC GGG GTG GGG GAG CAA AAA CTA   432
CAG TTC CCA GTC CTC GCT GCG CCG CCA CTG GGG CCG   468
GAG CCC AGG ACG CCA GGC CCC TCC TCT GGG GAG GAG   504
CCT ATG CGG GGG GCG GAG CTA GGA GGA GGT TGG AGA   540
GTT AAG CCA AGC AAT GAC CAG CTG CTA ATA AGT   576
GGG CTT GGC TTA CAA TGT AAC AGT GGC AGG AGG AGG   612
CGA GCG AAG CTA TTG AGC CAG CGA GGA GTG AAG TGA   648
GCC TGG *CCT CAC ACG CTC CTA GAG GAC CAC*            684
```
start of overlap with HSKCa3 cDNA sequence

HKCA3/KCNN3 SMALL CONDUCTANCE CALCIUM ACTIVATED POTASSIUM CHANNEL: A DIAGNOSTIC MARKER AND THERAPEUTIC TARGET

CROSS REFERENCE TO RELATED APPLICATIONS

This application is a continuation application of U.S. application Ser. No. 09/565,590 filed May 4, 2000, now issued as U.S. Pat. No. 6,653,100; which is a divisional application of U.S. application Ser. No. 09/115,446 filed Jul. 14, 1998, now issued as U.S. Pat. No. 6,165,719; which claims the benefit under 35 USC § 119(e) of U.S. application Ser. Nos. 60/070,741 filed Jan. 8, 1998 and 60/052,556 filed Jul. 15, 1997, both now abandoned. The disclosure of each of the prior applications is considered part of and is incorporated by reference in the disclosure of this application.

STATEMENT AS TO FEDERALLY SPONSORED RESEARCH

This invention was made with partial Government support under Grant No. GMOD54872, awarded by Organization USPHS. The government may have certain rights in the invention.

FIELD OF THE INVENTION

This invention relates generally to the field of small conductance calcium activated potassium channels, and more specifically to the diagnosis, study, prevention and treatment of disorders related to these channels.

BACKGROUND OF THE INVENTION

Action potentials in vertebrate neurons are followed by an after hyperpolarization (AHP) that may persist for several seconds and may have profound consequences for the neuronal firing pattern. The AHP has several components, which are distinct are mediated by different calcium activated potassium channels. Small conductance calcium activated potassium channels (SKCa, where "S" represents "small") underlie slow components of the AHP, which are responsible for spike-frequency adaption (Hotson, J. R., and Prince, D. A., *J. Neurophysiol.* 43:409, 1980). Small conductance channels have a unitary conductance of 4-14 ps, are exquisitely sensitive to internal $Ca^{2+}$, lack the property of voltage dependence and are blocked by nanomolar concentrations of the natural toxins apamin and scyllatoxin. These channels modulate the firing pattern of neurons via the generation of slow membrane afterhyperpolarizations (Nicoll, R. A., *Science* 241:545-551, 1988). The intermediate channels (IKCa, where "I" represents intermediate conductance) have a conductance of 11-40 pS, are blocked by charybdotoxin and clotrimazol, and are as sensitive to internal $Ca^{2+}$ as SKCa channels (Ishii, T. M., et al., *Proc. Natl. Acad. Sci. USA* 94:11651-11656, 1997; Joiner, W. J., et al., *Proc. Natl. Acad. Sci. USA* 94:11013-11018,1997).

Channel dysregulation, particularly of the glutamate receptor/channels, figures prominently in pathogenic mechanisms involved in many processes leading to neurodegeneration, such as strokes head trauma, and specific toxic drug reactions. Glutamate is the major excitatory neurotransmitter in the CNS, and while there are five known types of glutamate receptors, the NMDA-type ionotropic receptor/channel complex plays the most prominent role (Sucher, N. J., et al., *Trends in Pharmacological Sciences* 17:348-55, 1996; Kaku, D. A., et al., *Science* 260:1515-8, 1993). Overstimulation of the NMDA pathway produces calcium overload and the excitotoxic death of neurons (Choi, D. W., *Neuron* 1:623-34, 1988). The toxicity may arise through calcium-dependent proteases or through excessive signaling, perhaps leading to apoptosis. Extracellular $Mg^{2+}$ produces tonic block of the NMDA receptor/channel complex, and in the presence of its agonist, the receptor/channel conducts an inward sodium and calcium current only if the membrane potential is concurrently being depolarized (Choi, 1988, supra). (This paried input paradigm perhaps also forms an elementary unit in learning, another function subserved by this receptor/channel.) As the cytosolic calcium concentration rises, SKCa channels are activated, generating slow membrane afterhyperpolarizations (Nicoll, R. A., *Science* 241:545-551, 1988; Johnson, S. W., and Seutin, V., *Neuroscience Letters* 231:13-16, 1997). NMDA current is physiologically terminated by this membrane repolarization, which restores the magnesium block. Since SKCa channels regulate ion flow through the NMDA-receptor/channel complex, they play a critical role in dampening neural excitability, and may also contribute to the development of neurological diseases associated with functional alterations in the NMDA signaling pathway (Johnson and Seutin, 1997, supra).

The SKCa are currents that have been described in a wide range of tissues, including brain (Lancaster, B. and Nicoll, R. A., *J. Physiol.* 389:187-203, 1987), peripheral neurons (Goh, J. W., and Pennefather, P. S., *J. Physiol.* 394:315-330, 1987), skeletal muscle (Romey, G., and Lazdunski, M., *Biochem. Biophys. Res. Commun.* 118:669-674, 1984) adrenal chromaffin cells (Neely, A., and Lingle, C. J., *J. Physiol.* 452:97-131, 1992), leukocytes (Grissmer, S., et al., *J. Gen. Physiol.* 99:63-84, 1992), erythrocytes (Hamill, O. P., *J. Physiol.* 319:97P-98P, 1981), colon (Lomax, R. B., et al., *Gut* 38:243-247, 1996), and airway epithelia (Welsh, M. J., and McCann, J. D., *Proc. Natl. Acad Sci. USA* 82:8823-8826, 1985). Certain types of SKCa channels have been distinguished by their sensitivities to the bee venom apamin, whereas other functionally related conductances appear insensitive (Sah, P., and AcLachlan, E. M., 1992, *J. Neurophysiol.* 74:1772-1776). The distinguishing features of the SKCa channels from the maxi-K calcium activated (BK) potassium channels are the SKCa channels' low conductance (less than 50 pS), the weak or negligible dependence of their activity on membrane voltage, and their high affinity for calcium ($EC_{50}$<1 µM) (e.g., Lancaster, B., and Zucker, R. S., *J. Physiol.* 475:229-239, 1994).

Recently, Imbert et al. reported the cloning of six novel cDNAs, each containing one or more long CAG repeats. These cDNAs were isolated from a lymphoblastoid cell cDNA expression library generated from patients with autosomal dominant cerebellar ataxia with a monoclonal antibody specific for polyglutamine sequences (Imbert et al., *Nature Genetics* 14:285, 1996). One of the cDNAs, designated AAD14, encoded the partial sequence of a putative protein of 228 amino acids in length. This polypeptide of unknown function contained two long polyglutamine stretches.

Kohler et al. first described a rat small conductance calcium activated potassium channel (rSKCa3) gene, and published the truncated form of the gene (Kohler et al., *Science* 274:1709, 1996). An alignment of the known members of the small conductance calcium-activated potassium channels was described by Joiner et al. (*Proc. Natl. Acad. Sci.* 94:1 1013, 1997), who cloned the hSK4 gene, using the potassium channel signature sequence (XXTXGYG, SEQ ID NO:9). Ishii et al. (*Proc. Natl. Acad. Sci. USA* 94:11651-6, 1997) further cloned an intermediate conductance calcium-activated potassium channel (h1K1).

Schizophrenia is a chronic disabling disorder with a lifetime morbid risk of 1% in the general population. The illness has a significant genetic component (Kendler, K. S., In: *Relatives at Risk for Mental Disorders*, Dunner, D. L., Gershon, E. S., and Barrett, J. E. (eds), Raven Press, New York, pp. 247-263, 1988) and often develops in early adulthood. The disease is characterized by a constellation of symptoms including hallucinations and delusions, disordered thinking and concentration, inappropriate emotional responses, catatonia, erratic behavior, and social and occupational deterioration. Although still controversial, "anticipation" (an increase in severity through successive generations) has been found in studies of affected families (Bassett, A. S., and Honer, W. G., *Am. J. Hum. Genet.*, 54:864-870, 1994). Trinucleotide repeat expansions have been found to underlie several Mendelian hereditary neurological diseases (Ashley, C. T., Jr., and Warren, S. T., *Annu. Rev. Genet.*, 29:703-728, 1995; Timchenko, L. T., and Caskey, C. T., *FASEB J.*, 10:1589-1597, 1996; among others).

Several human hereditary neurological diseases, such as Huntington's disease, fragile X syndrome, myotonic dystrophy, spinal and bulbar muscular atrophy, Machado-Joseph disease, Friedrich's disease and spinocerebellar ataxia, are associated with expanded trinucleotide repeats (typically >35) within the coding region (e.g., Timchenko, L. T., and Caskey, C. T., *FASEB J.* 10:1589-97, 1996; Hannan, A. J., *J. Clin. Exp. Pharm. Physiol.* 23:1015-20, 1996; Bates, G., *Bioessays* 18:175-8, 1996), untranslated sequences (e.g., Warren, S. T., and Ashley, C. T., *Ann. Rev. Neurosci.* 18:77-99, 1995; Tsilfidis, C., et al., *Nature Genet.* 1 :192-195, 1992), or introns (Campuzano, V., et al., *Science* 271:1423-7, 1996) of genes. An association has been shown between the presence of anonymous CAG/CTG repeats and the development of schizophrenia and bipolar disease (O'Donovan, M. C., et al., *Nature Genetics* 10:380-1, 1995; O'Donovan et al., *Psychological Med.* 26:1145-1153, 1996; Cardino, A. G., et al., *Brit. J. Psychiatry* 169:766-771, 1996).

Intergenerational lengthening of such repeats is thought to underlie the phenomenon of "anticipation" (Ashley and Warren, 1995, supra) observed in schizophrenia and bipolar disease, wherein the disease worsens with subsequent generations (Johnson, J. E., et al., *Amer. J Med. Genet.* 75:275-280, 1997; Lipp, O., et al., *Psychiatric Genet.* 5: S8, 1995; Serbanescu-Grigorow, M., et al., *Psychiatric Genet.* 5:S10, 1995). The subset of these mutations caused by expansions of the CAG trinucleotide have been found only within the coding region of genes, and the encoded polyglutamine arrays may occur in different places within the open-reading-frame (Housman, D., *Nature Genet.* 10:3-4., 1995). In the past few years, expanded "anonymous" CAG repeats in unidentified genes have been reported in patients with schizophrenia, with considerable overlap between allele distributions in patients and controls (O'Donovan, M. C., et al., *Nature Genetics* 10:380-381, 1995; Morris, A. G., et al., *Hum. Mol. Genet.*, 4:1957-1961, 1995; O'Donovan, M. C., et al., *Psychol. Med.* 26:1145-1153, 1996; O'Donovan, M. C., and Owen, M. J., *Psychol. Med.* 26:1-6, 1996; O'Donovan, M. C., and Owen, M. J., *Annals Med.* 28:541-546, 1996a).

SUMMARY OF THE INVENTION

The present invention is based on the discovery and cloning of the human small conductance calcium activated potassium channel type 3 (hKCa3/KCNN3) gene, which is expressed in neuronal cells, skeletal muscle, heart, and lymphocytes. Alterations in the hKCa3/KCNN3 gene or its protein product may enhance susceptibility to schizophrenia and/or bipolar disorder. Activators of this channel may be useful as neuroprotective agents (e.g., for preventing stroke or reducing neuronal injury following head trauma) via the "physiological" inactivation of NMDA-receptor-mediated excitotoxic mechanisms. In addition, since hKCa3/KCNN3 is expressed in lymphocytes, the channel may play a role in modulating calcium-signaling during the immune response. The gene is expressed in skeletal muscle and the heart where it may play a similar role in modulating signaling. Thus hKCa3/KCNN3 may be involved in neuropsychiatric, neurological, neuromuscular, and immunological disorders.

In a first embodiment, substantially purified hKCa3/KCNN3 polypeptide and isolated polynucleotides encoding hKCa3/KCNN3 polypeptides are provided. Antibodies which bind to hKCa3/KCNN3 polypeptides are also disclosed.

In another embodiment, a method for identifying a compound which affects hKCa3/KCNN3 polynucleotide or polypeptide is provided. Such compounds include drugs and small molecules.

A method for diagnosis of a subject having or at risk of having a hKCa3/KCNN3-associated disorder is also provided. A method of determining the prognosis of a subject with an hKCa3/KCNN3-associated disorder is disclosed.

In another embodiment, a method of treating a subject having or at risk of having an hKCa3/KCNN3-associated disorder by administering a therapeutically effective amount of a polynucleotide encoding SEQ ID NO:2 is also provided. A method of treating a patient having or at risk of having an hKCa3/KCNN3-associated disorder by introducing into a cell of the patient a nucleotide sequence encoding SEQ ID NO:2 under the control of a eukaryotic promoter so that the cell expresses SEQ ID NO:2 is provided.

A composition for administration of hKCa3/KCNN3 to a patient of a therapeutically effective amount of hKCa3/KCNN3 polypeptide is disclosed.

In an additional embodiment, a kit useful for detecting the presence of hKCa3/KCNN3 polypeptide in a sample from a subject having a hKCa3/KCNN3-associated disorder is provided. A kit useful for the detection of polynucleotide encoding hKCa3/KCNN3 in a subject having a hKCa3/KCNN3 associated disorder is also provided.

In a further embodiment, transgenic nonhuman animals having a transgene encoding hKCa3/KCNN3 are also described.

BRIEF DESCRIPTION OF THE DRAWINGS

FIGS. 1A-1D show the alignment of the nucleotide sequences of AAD14 (human cDNA; truncated; accession # Y08263, SEQ ID NO:3), STS-G16005 (human genomic; complete, SEQ ID NO:4), our human genomic sequence (SEQ ID NO:5), rat SKCa3 (cDNA; truncated; accession #U69884, SEQ ID NO:6), EST AA285078 (SEQ ID NO:7), and our human brain cDNA sequence (SEQ ID NO:1). The two stretches of the trinucleotide repeats are bracketed. The two premature stop codons in the sequence are underlined and shown by a double asterisk (**). The two additional thymidines in the AAD14 sequence are in bold and underlined. The putative start codon for the rat SKCa3 sequence is bold and underlined. The additional nucleotide in AAD14 responsible for the frame shift is underlined, bold and shown by an asterisk (*).

FIGS. 2A-2B shows the alignment of the amino acid sequences of rat SKCa3 (SEQ ID NO:8) and the two apparent reading frames (Fr 1; Fr 2) within hKCa3/KCNN3 (SEQ ID NO:2). The putative transmembrane segments are highlighted, and so is the pore sequence. The polyglutamine arrays are in bold.

FIG. 3A shows the results for Ashkenazi and Sephardic Jews combined. FIG. 3B shows the results for Ashkenazi Jews only. FIG. 3C shows the results for Sephardic Jews only. FIG. 3D shows a comparison for only the longer allele from all subjects. FIG. 3E shows a comparison for only the shorter allele from all subjects. The number of subjects in each category is indicated in parentheses. Using of the Wilcoxon rank-sum test to compare each of the patient distributions (solid bars) with ethnically matched controls (stippled bars) yielded the indicated p-values.

FIG. 4A and FIG. 4B. show the results from patients diagnosed as suffering from (FIG. 4A) "paranoid" (DSM-IV 295.3) or (FIG. 4B) "residual" (DSM-IV 295.6) types of schizophrenia. FIG. 4C shows the results from non-affected controls. Arrows indicate the median value for each distribution. Pairwise comparisons using the Wilcoxon rank-sum test showed a significant difference between the distributions of the shorter alleles of the "paranoid" and "residual" diagnosis groups (panel A versus B, p=0.0049), and between those of the "paranoid" diagnosis group and the controls (panel A versus C, p=$2.1\times10^{-6}$).

FIGS. 5A-D show the nucleotide sequence of hKCa3/KCNN3 cDNA. The 3' end of the message is marked by the poly-A region, following the poly-A signal sequence (AATAAA) which overlaps the termination codon.

FIG. 6 shows the genomic nucleotide sequence of hKCa3/KCNN3 showing the boundary between the exon, containing both N-terminal CAG/polyglutamine repeats, and the following intervening sequence.

FIG. 8 shows the genomic nucleotide sequence upstream of the known cDNA sequence of hKCa3/KCNN3. The region of overlap with the cDNA is shown in bold.

DESCRIPTION OF THE PREFERRED EMBODIMENTS

Figure 3:
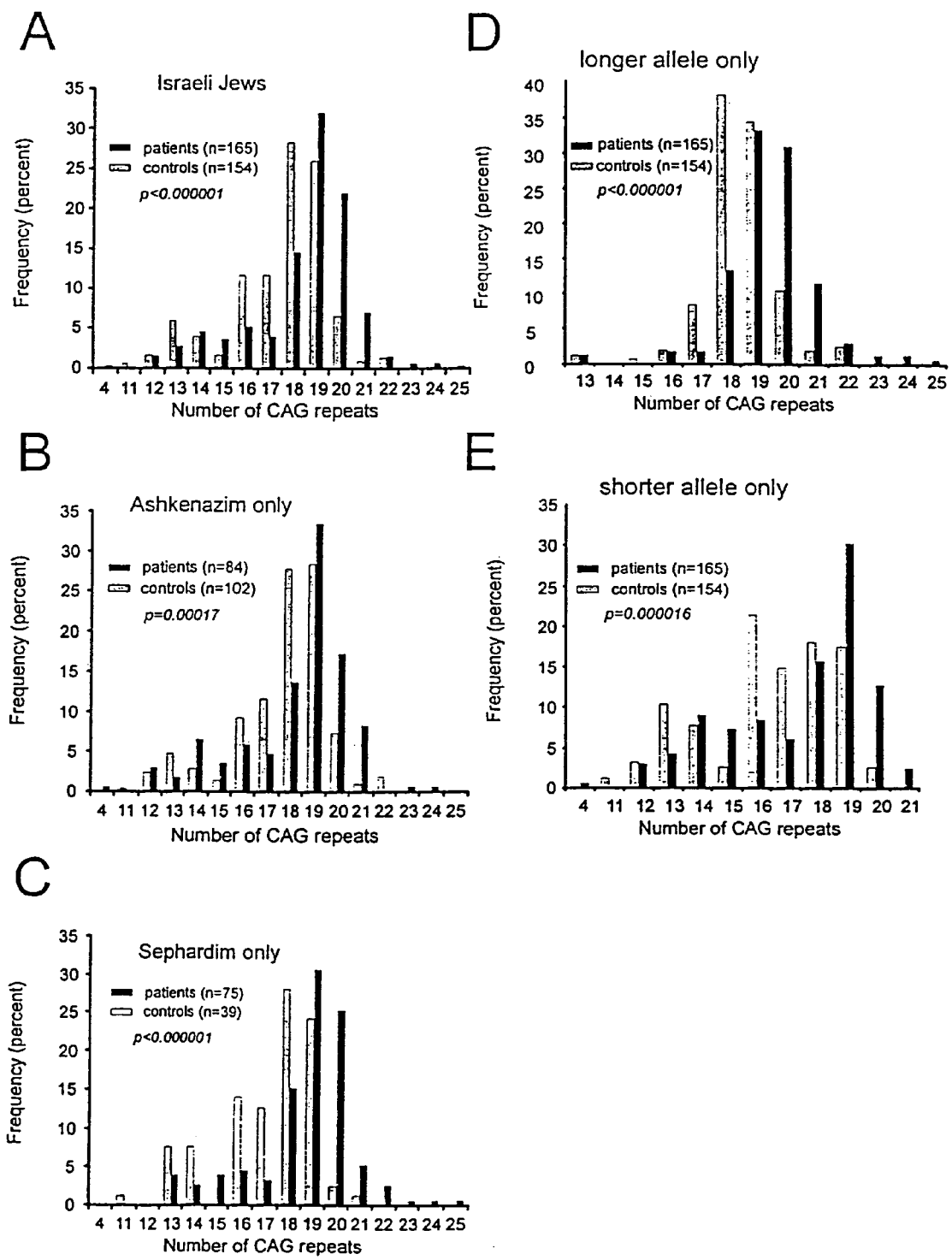
FIGS. 3A-3E is a series of graphs illustrating the distribution of CAG repeat lengths in hKCa3/KCNN3 in schizophrenia patients and controls among Israeli Jews. Ordinate shows the frequency of occurrence for all alleles of the numbers of repeats indicated on the abscissa.

The present invention relates to hKCa3/KCNN3 and to the use of hKCa3/KCNN3 antibodies, nucleic acid sequences, and amino acid sequences in the study, diagnosis, prevention and treatment of hSKCa-associated disorders, including neuropsychiatric, neurological, neuromuscular, and immunological disorders.

Polynucleotides and Polypeptides

In one embodiment, the invention provides substantially purified hKCa3/KCNN3 polypeptide. Preferably, hKCa3/KCNN3 has an amino acid sequence set forth in SEQ ID NO:2. The term "substantially purified" as used herein refers to a polypeptide which is substantially free of other proteins, lipids, carbohydrates or other materials with which it is naturally associated. One skilled in the art can purify hKCa3/KCNN3 using standard techniques for protein purification. The substantially pure polypeptide will yield a single major band on a non-reducing polyacrylamide gel. The purity of the hKCa3/KCNN3 polypeptide can also be determined by amino-terminal amino acid sequence analysis.

Minor modifications of the hKCa3/KCNN3 primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity of the hKCa3/KCNN3 still exists.

The polypeptides of the invention also include dominant negative forms of the hKCa3/KCNN3 polypeptide which do not have the biological activity of hKCa3/KCNN3. A "dominant negative form" of hKCa3/KCNN3 is a polypeptide that is structurally similar to hKCa3/KCNN3 but does not have wild-type hKCa3/KCNN3 function. For example, a dominant-negative hKCa3/KCNN3 polypeptide may interfere with wild-type hKCa3/KCNN3 function by binding to, or otherwise sequestering, regulating agents, such as upstream or downstream components, that normally interact functionally with the hKCa3/KCNN3 polypeptide.

The invention provides polynucleotides encoding the hKCa3/KCNN3 protein as well as genomic DNA sequences. These polynucleotides include DNA, cDNA and RNA sequences which encode hKCa3/KCNN3. It is understood that all polynucleotides encoding hKCa3/KCNN3 are also included herein, as long as they encode a polypeptide with hKCa3/KCNN3 activity. Such polynucleotides include naturally occurring, synthetic, and intentionally manipulated polynucleotides. For example, hKCa3/KCNN3 polynucleotide may be subjected to site-directed mutagenesis. The polynucleotide sequence for hKCa3/KCNN3 also includes antisense sequences, and sequences encoding dominant negative forms of hKCa3/KCNN3. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of hKCa3/KCNN3 polypeptide encoded by the nucleotide sequence is functionally unchanged.

Figure 7:
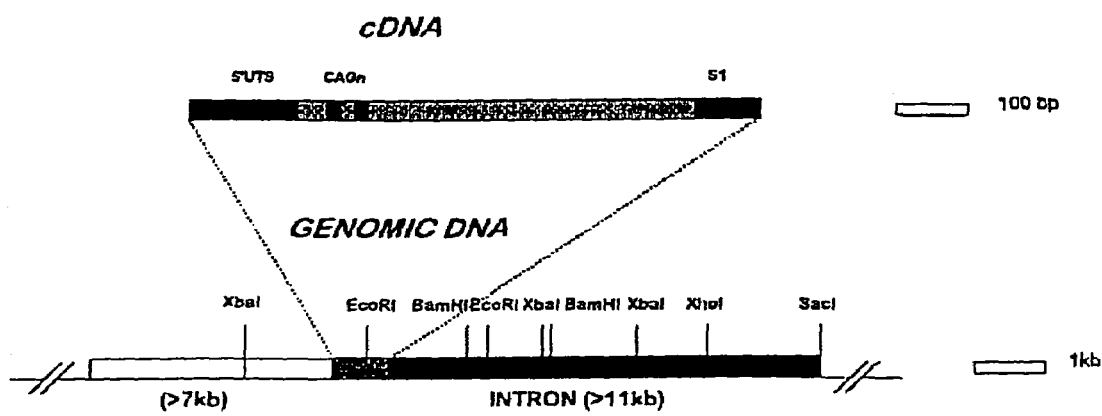
FIG. 7 is a schematic diagram of genomic region containing the first exon of hKCa3/KCNN3.

Specifically disclosed herein is a polynucleotide sequence containing the hKCa3/KCNN3 gene as well as the genomic DNA sequence (FIG. 7). Preferably, the hKCa3/KCNN3 nucleotide sequence is SEQ ID NO:1. The term "polynucleotide" or "nucleic acid sequence" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double forms of DNA.

The polynucleotide encoding hKCa3/KCNN3 includes SEQ ID NO:1, dominant negative forms of hKCa3/KCNN3, and nucleic acid sequences complementary to SEQ ID NO:1. A complementary sequence may include an antisense nucleotide. When the sequence is RNA, the deoxynucleotides A, G, C, and T of SEQ ID NO:1 are replaced by ribonucleotides A, G, C, and U, respectively. Also included in the invention are fragments of the above-described nucleic acid sequences that are and are at least 15 bases in length, which is sufficient to permit the fragment to selectively hybridize to DNA that encodes the protein of SEQ ID NO:2 under physiological conditions or a close family member of hKCa3/KCNN3. The term "selectively hybridize" refers to hybridization under moderately or highly stringent conditions which excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

The nucleotide sequence encoding the hKCa3/KCNN3 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Given the extensive conservation of amino acid sequences between species, it would now be routine for one of skill in the art to obtain the small conductancd calcium activated potassium channel nucleic acid and amino acid sequence from any species, including those provided herein (i.e., rat and human). For example, it is believed that other primate nucleic acid and amino acid sequences are now readily obtainable using the hKCa3/KCNN3 sequence of the invention or fragments thereof as a probe. One of skill in the art can determine the percentage of sequence identity between species by aligning the encoded amino acid sequences, determining the corresponding alignment of the encoding polynucleotides, and then counting the number of residues shared between the sequences being compared at each aligned position. No penalty is imposed for the presence of insertions or deletions, but insertion or deletions are permitted only where required to accommodate an obviously increased number of amino acid residues in one of the sequences being aligned. Offsetting insertions just to improve sequence alignment are not permitted at either the polypeptide or polynucleotide level. Thus, any insertions in the polynucleotide sequence will have a length which is a multiple of 3. The percentage is given in terms of residues in the test sequence that are identical to residues in the comparison reference sequence.

Percent identify is calculated for oligonucleotides of this length by not allowing gaps in either the oligonucleotide or the polypeptide for purposes of alignment. Throughout this disclosure, whenever at least one of two sequences being compared is a degenerate oligonucleotide comprising an ambiguous residue, the two sequences are identical if at least one of the alternative forms of the degenerate oligonucleotide is identical to the sequence with which it is being compared. As an illustration, AYAAA is 100% identical to ATAAA, since AYAAA is a mixture of ATAAA and ACAAA. Methods to determine the homology and percent identity of sequences are well known in the art. These methods can be performed manually (using mathematical calculations) or with a computer program, such as BLAST (Altschul et al., 1986, Bull. Math. Bio. 48:603-616).

DNA sequences encoding hKCa3/KCNN3 can be expressed in vitro by DNA transfer into a suitable host cell. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the hKCa3/KCNN3 polynucleotide sequences may be inserted into an expression vector. The term "expression vector" refers to a plasmid, virus or other vehicle known in the art that has been manipulated by insertion or incorporation of the hKCa3/KCNN3 genetic sequences. Polynucleotide sequence which encode hKCa3/KCNN3 can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., *Methods in Enzymology* 153:516-544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the polynucleotide encoding hKCa3/KCNN3 may be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedron promoters).

Polynucleotide sequences encoding hKCa3/KCNN3 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

By "transformation" is meant a genetic change induced in a cell following incorporation of new DNA (i.e., DNA exogenous to the cell). Where the cell is a mammalian cell, the genetic change is generally achieved by introduction of the DNA into the genome of the cell (i.e., stable).

By "transformed cell" is meant a cell into which (or into an ancestor of which) has been introduced, by means of recombinant DNA techniques, a DNA molecule encoding hKCa3/KCNN3. Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the hKCa3/KCNN3 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

Antibodies

The hKCa3/KCNN3 polypeptides of the invention can be used to produce antibodies which are immunoreactive or bind to epitopes of the hKCa3/KCNN3 polypeptides. Antibodies which consist essentially of pooled monoclonal antibodies with different epitopic specificities, as well as distinct monoclonal antibody preparations are provided.

The preparation of polyclonal antibodies is well-known to those skilled in the art. See, for example, Green et al., "Production of Polyclonal Antisera," in: *Immunochemical Protocols* pages 1-5, Manson, ed., Humana Press 1992; Coligan et al., "Production of Polyclonal Antisera in Rabbits, Rats, Mice and Hamsters," in: *Current Protocols in Immunology*, section 2.4.1, 1992, which are hereby incorporated by reference.

The preparation of monoclonal antibodies likewise is conventional. See, for example, Kohler & Milstein, *Nature* 256:495, 1975; Coligan et al., sections 2.5.1-2.6.7; and Harlow et al., in: *Antibodies: a Laboratory Manual*, page 726, Cold Spring Harbor Pub., 1988, which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., "Purification of Immunoglobulin G (IgG)," in: *Methods in Molecular Biology*, Vol. 10, pages 79-104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465, 1991, and Losman et al., *Int. J. Cancer* 46:310, 1990, which are hereby incorporated by reference.

Alternatively, a therapeutically useful anti-hKCa3/KCNN3 antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989, which is hereby incorporated in its entirety by reference. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immunol.* 150:2844, 1993, which are hereby incorporated by reference.

Antibodies of the invention also may be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994, which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994, which are hereby incorporated by reference.

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be ftrther cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisonhoffel al., Arch. Biochem. Biophys. 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA* 69:2659, 1972. Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: a Companion to Methods in Enzymolog*, Vol. 2, page 97, 1991; Bird et al., *Science* 242:423426, 1988; Ladner et al., U.S. Pat. No. 4,946,778; Pack et al., *Bio/Technology* 11:1271-77, 1993; and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: a Companion to Methods in Enzymology*, Vol. 2, page 106, 1991.

Antibodies which bind to the hKCa3/KCNN3 polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Method for Identifying Compounds which Affect hKCa3/KCNN3

The invention provides a method for identifying a compound which can modulate hKCa3/KCNN3 activity. Drugs that modulate other ion channels have already had a major impact in the treatment of common diseases, as they provide the primary means to treat cardiac arrhythmias, epilepsy, hypertension, diabetes, and stroke. Furthermore, many current drugs are useful primarily because they indirectly modulate potassium channels. The method includes incubating compounds and a sample containing hKCa3/KCNN3 polypeptide or polynucleotide under conditions sufficient to allow the components to interact, and measuring the effect of the compound on the expression or activity of hKCa3/KCNN3. In one embodiment, the sample is a cell expressing hKCa3/KCNN3 polypeptide or polynucleotide. The activity of hKCa3/KCNN3 in the sample can then be compared to the hKCa3/KCNN3 activity of a control sample not incubated with the compound. Alternatively, the effect of the compound on a signaling event (e.g., an ion flux) can be evaluated.

A "second messenger response" or "signaling event" means the generation of a biochemical or physiological response as a result of contacting the compound with a sample containing hKCa3/KCNN3 polypeptide or polynucleotide . In general, a signaling event results in the change of a molecular characteristic or parameter of the cell. Nonlimiting examples include ion fluxes (e.g., a potassium flux), enzyme activation (e.g., a serine/threonine kinase), changes in cyclic nucleotides (e.g., cAMP, cADP, cGMP, cGDP, etc.), among others. A specific, nonlimiting example of a signaling event is the generation of a $K^+$ flux following the interaction of a compound with hKCa3/KCNN3.

The effect of the compound on hKCa3/KCNN3 can. be measured by assessing the expression of hKCa3/KCNN3 by methods well known in the art (e.g., Northern blots, see example 7). Alternatively, the effect of the compound on the activity of hKCa3/KCNN3 can be assessed by measuring the signaling event by any means known to one of skill in the art. In one embodiment, the electrophysiological properties of a cell expressing hKCa3/KCNN3 polynucleotide or polypeptide can be measured. For example, in order to determine the effect of the compound on the activity of hKCa3/KCNN3, the $Ca^{2+}$ dependent, $K^+$ selective current can be measured as whole cell current from a single cell, or in membrane patches. Single channel recordings can also be used.

Alternatively, a "physiological indicator" can be used to measure the signaling event. A "physiological indicator" is any compound in which a measurable property changes in a response to a physical parameter of the cell. Cell signaling events that occur in vivo can be of very short duration. The physiological indicators can allow measurement of the physiological parameter over the same time period that the event actually occurs, or after the event occurs (over a longer time period). One nonlimiting example of a measurable property is a change is in fluorescence of an physiological indicator in response to an ion flux.

Fluorescence is one spectral property of which can be used as the means of detecting a physiological parameter of a cell. As used herein, the term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between a cell contacted with a compound of interest as compared to a control cell suffices to identify a compound which can modulate hKCa3/KCNN3 activity. A measurable difference can be determined by determining the amount of any quantitative fluorescent property, e.g., the amount of fluorescence at a particular wavelength, or the integral of fluorescence over the emission spectrum. Optimally, the physiological indicator is selected to have fluorescent properties that are easily distinguishable.

A second nonlimiting example is a change in the physical location of the indicator. Movement of the indicator can be measured by means well known to one of skill in the art. For example, fluorescence activated cell sorting can be used to identify exclusion or uptake of a physiological indicator.

The compounds which affect hKCa3/KCNN3 include peptides, polypeptides, chemical compounds and biological agents. Psychotropic, antiviral, and chemotherapeutic compounds can be tested using the method of the invention. "Incubating" includes conditions which allow contact between the test compound and the hKCa3/KCNN3. "Contacting" includes in solution and solid phase. The test compound may also be a combinatorial library for screening a plurality of compounds. Compounds identified in the method of the invention can be further evaluated, detected, cloned, sequenced, and the like, either in solution of after binding to a solid support, by any method usually applied to the detection of a specific DNA sequence, such as PCR, oligomer restriction (Saiki et al., *Bio/Technology* 3:1008-1012, 1985), allele-specific oligonucleotide (ASO) probe analysis (Conner et al., *Proc. Natl. Acad Sci. USA* 80:278, 1983), oligonucleotide ligation assays (OLAS) (Landegren et al., *Science* 241:1077, 1988), and the like. Molecular techniques for DNA analysis have been reviewed (Landegren et al., *Science* 242:229-237, 1988).

A compound can affect hKCa3/KCNN3 by either stimulating or inhibiting hKCa3/KCNN3. A compound "inhibits" hKCa3/KCNN3 if the ability to transport potassium is decreased. A compound "stimulates" hKCa3/KCNN3 if the ability to transport potassium is increased.

The sample can be any sample of interest. The sample may be a cell sample or a membrane sample prepared from a cell sample. Suitable cells include any host cells containing a recombinant hKCa3/KCNN3 vector of the invention. Preferably, the host cells functionally express the hKCa3/KCNN3 polypeptide, but preferably have low background potassium conductance. Alternatively, cell lines expressing hKCa3/KCNN3 polypeptide can be used. For example, Rajii or K562 cells can be used (see Example 7).

In one embodiment, by employing a competition between an agonist and a compound of interest, absence of a signaling event will indicate the presence of an antagonist. These assays are well known in the literature.

The binding affinities of compounds which affect hKCa3/KCNN3 can also be determined in either cells or a membrane preparation expressing hKCa3/KCNN3. In these assays, a labeled ligand is employed. A number of labels have been indicated previously (e.g., radiolabels, fluorescence labels, among others) to be of use. The candidate compound is added in an appropriate buffered medium. After an incubation to ensure that binding has occurred, the surface may be washed free of any nonspecifically bound components of the assay medium, particularly any nonspecifically bound labeled ligand, and any label bound to the surface determined. The label may be quantitatively measured. By using standards, the relative binding affinity of a candidate compound can be determined.

The antibodies and polynucleotides of the invention can be used to detect or treat a hKCa3/KCNN3-associated disorder or an hKCa3/KCNN3-related disorder. The term "hKCa3/KCNN3-associated disorder" denotes neuropsychiatric as well as non-neuropsychiatric disorders (e.g., neurological, neuromuscular, and immunological disorders, among others) having a clinical appearance similar to or distinguishable from that produced by disorders in hKCa3/KCNN3 function itself. These disorders may be understood to be caused by defects in other molecules known to participate in signaling pathways influenced by hKCa3/KCNN3, or may still have no known molecule correlate. For example, it may be that only some patients with schizophrenia have abnormal hKCa3/KCNN3 function, while others with an identical syndrome have normal hKCa3/KCNN3 function (their syndrome presumably produced by other genetic factors). A "neuropsychiatric" disorder is a human behavior disorder (see *The Merck Manual of Diagnosis and Therapy*, 16th edition, p. 1532, Robert Berkow et al. (eds), Merck Research Laboratories, New Jersey, 1992). Examples of psychiatric disorders are the "schizophrenic disorders," which are mental disorders with a tendency toward chronicity, which impair functioning and are characterized by psychotic symptoms involving disturbances of thought, perception feeling, and behavior. Another example of a psychiatric disorder is a "mood disorder" which is characterized by a pervasive disturbance of mood, wherein a "mood" is a sustained emotion. A "bipolar disorder" is a mood disorder having depressive and elated or excited periods.

The invention can be used to determine the prognosis of a hKCa3/KCNN3-associated disorder. It may also be useful in guiding choices between different treatment regimens in patients with hKCa3/KCNN3-associated or -related disorders. The "prognosis" is a forecast as to the probable outcome of an attack of a disease; the prospect as to recovery from a disorder as indicated by the nature and symptoms of the case. In addition, the invention may be used to identify or treat individuals who are "at risk" of developing a hKCa3/KCNN3-associated disorder. These individuals may be identified by a method of the invention for detecting the presence or absence of hKCa3/KCNN3 or by any other diagnostic means, and/or may be treated by a method of the invention, prior to the actual onset of the clinical appearance of disorder. The "clinical appearance" can be any sign or symptom of the disorder.

Essentially, any disorder which is etiologically linked, as either an hKCa3/KCNN3-associated or hKCa3/KCNN3-related disorder, to increased expression of hKCa3/KCNN3 could be considered susceptible to treatment with a hKCa3/KCNN3 suppressing reagent, and any disorder which is etiologically linked, as either an hKCa3/KCNN3-associated or hKCa3/KCNN3-related disorder, to decreased expression of hKCa3/KCNN3 could be considered susceptible to treatment with hKCa3/KCNN3 activating reagents, including treatments with polynucleotides encoding hKCa3/KCNN3 or the hKCa3/KCNN3 polypeptide itself.

For purposes of the invention, an antibody or nucleic acid probe specific for hKCa3/KCNN3 may be used to detect hKCa3/KCNN3 polypeptide (using antibody) or polynucleotide (using nucleic acid probe) in subject samples such as biological fluids, cells, tissues, or nucleic acid. Any specimen containing a detectable amount of antigen or polynucleotide can be used. Examples of biological fluids of use with the invention are blood, serum, plasma, urine, mucous, and saliva. Tissue or cell samples can also be used with the subject invention. The samples can be obtained by many methods such as cellular aspiration, or by surgical removal of a biopsy sample.

The invention provides a method for detecting hKCa3/KCNN3, for example, which comprises contacting an hKCa3/KCNN3 antibody or nucleic acid probe with a cell suspected of expressing the hKCa3/KCNN3 and detecting binding to the antibody or nucleic acid probe. The antibody reactive with the hKCa3/KCNN3 or the nucleic acid probe is preferably labeled with a compound which allows detection of binding to hKCa3/KCNN3. The level of the hKCa3/KCNN3 in the subject cell can be compared with the level in a cell not affected by the disease process. The cell not affected by the disease process can be taken from the same subject, or can be from a control subject not affected by the disease process, or can be from a cell line. Preferably the subject is human. One can distinguish the alleles of hKCa3 that are expressed, e.g., different CAG repeat lengths, point mutations.

When the cell component is nucleic acid, it may be necessary to amplify the nucleic acid prior to binding with the hKCa3/KCNN3 specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Those of skill in the art will know, or can readily discern, an appropriate immunoassay format without undue experimentation.

The antibodies of the invention can be bound to many different carriers, both soluble and insoluble, and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The monoclonal antibodies or polynucleotides of the invention can be used in vitro and in vivo to monitor the course of amelioration of a hKCa3/KCNN3-associated disease in a subject. Thus, for example, by measuring the increase or decrease in the number of cells expressing antigen comprising a polypeptide of the invention or changes in the concentration of such antigen present on cells or in various body fluids, it would be possible to determine whether a particular therapeutic regimen aimed at ameliorating the hKCa3/KCNN3-associated disease is effective. The term "ameliorate" denotes a lessening of the detrimental effect of the hKCa3/KCNN3-associated disease in the subject receiving therapy.

Therapeutic Techniques

The present invention identifies a polynucleotide sequence that can be expressed in an altered manner as compared to expression in a normal cell, therefore it is possible to design appropriate therapeutic or diagnostic techniques directed to this sequence. The antibodies and polynucleotides of the invention can be used to detect or to treat an hKCa3/KCNN3-associated disorder.

Detection of elevated levels of hKCa3/KCNN3 expression is accomplished by hybridization of nucleic acids isolated from a cell of interest with an hKCa3/KCNN3 polynucleotide of the invention. Analysis, such as Northern Blot analysis, are utilized to quantitate expression of the hKCa3/KCNN3. Other standard nucleic acid detection techniques will be known to those of skill in the art.

Treatment can include modulation of hKCa3/KCNN3 gene expression and hKCa3/KCNN3 activity by administration of a therapeutically effective amount of a reagent that modulates the hKCa3/KCNN3. The term "modulate" envisions the suppression of expression of hKCa3/KCNN3 when it is overexpressed, or augmentation of the expression of hKCa3/KCNN3 when it is underexpressed. Where a disorder is associated with the decreased expression of hKCa3/KCNN3, nucleic acid sequences that encode hKCa3/KCNN3 can be used. Where a disorder is associated with the increased expression of hKCa3/KCNN3, nucleic acid sequences that interfere with the expression of hKCa3/KCNN3 can be used. This approach utilizes, for example, antisense nucleic acid, ribozymes, or triplex agents to block transcription or translation of hKCa3/KCNN3 mRNA, either by masking that mRNA with an antisense nucleic acid or triplex agent, or by cleaving it with a ribozyme.

Agents that block NMDA-type glutamate receptor/channels, such as ketamine, phencyclidine, and MK-801 (an experimental drug designed to be protective against excitotoxicity), induce a schizophrenia-like syndrome (Olney, J. W., and Farber, N. B., *Arch Gen Psych* 52:998-1007, 1995; Moghaddam, B., et al., *J. Neurosci.* 17:2921-7, 1997; Hirsch, S. R., et al., *Pharmacology, Biochemistry and Behavior* 56:797-802, 1997; Yamamoto, J., *Psychopharmacology* 131:379-87, 1997). In contrast, many antipsychotic drugs exert an activating, agonist-like effect on NMDA receptors, either directly or in a dopamine-dependent fashion (Banerjee, S. P., et al., *Neuroreport* 6:2500-4, 1995). In addition, drugs used to treat bipolar disorder type I (BPD-I), lithium and valproate, stimulate glutamate release and activate NMDA-receptors (Dixon, J. F., and Hokin, L. E., *Proc. Natl. Acad. Sci. USA* 94:4757-60,1997). Based on these findings, it has been suggested that hypofunction of the NMDA-receptor signaling pathway may contribute to the pathophysiology of both schizophrenia and BPD-I (Olney and Farber, 1995, supra; Hirsch et al., 1997, supra; Ishimaru, M., et al., *Trends in Neurosciences* 19:416-7,1996).

Without being bound by theory, since the physiological mechanism responsible for turning off NMDA activity is a SKCa current (Nicoll, R. A., *Science* 241:545-551, 1988;

Johnson, S. W., and Seutin, V., *Neuroscience Letters* 231: 13-16, 1997), enhanced activity of such a potassium channel might play such a role. Increased activity would excessively hyperpolarize the membrane, induce $Mg^{2+}$-dependent block of the NMDA-receptor, diminishing its activity. This would effectively suppress signaling via this pathway. By decreasing SKCa current, by inhibiting hKCa3/KCNN3, NMDA activity could be increased.

Antisense nucleic acids are DNA or RNA molecules that are complementary to at least a portion of a specific mRNA molecule (Weintraub, *Scientific American* 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target hKCa3/KCNN3-producing cell. The use of antisense methods to inhibit the in vitro translation of genes is well known in the art (Marcus-Sakura, *Anal.Biochem*. 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev*. 1(3):227, 199 1; Helene, C., *Anticancer Drug Design* 6(6):569), 1991.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn*. 260:3030, 1988). A major advantage of this approach is that, because they are sequence-specific, only mRNAs with particular sequences are inactivated.

There are two basic types of ribozymes namely, tetrahymena-type (Hasselhoff, *Nature* 334:585, 1988) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that the sequence will occur exclusively in the target mRNA species. Consequently, hanumerhead-type ribozymes are preferable to tetrahymena-type ribozymes for inactivating a specific mRNA species and 18-based recognition sequences are preferable to shorter recognition sequences.

The present invention also provides gene therapy for the treatment of disorders which are associated with hKCa3/KCNN3 protein. Such therapy would achieve its therapeutic effect by introduction of a therapeutic polynucleotide into cells having the disorder. The "therapeutic polynucleotide" may be polynucleotide sequences encoding hKCa3/KCNN3, or antisense polynucleotide specific for hKCa3/KCNN3, designed to treat a hKCa3/KCNN3-associated disorder. Delivery of the therapeutic polynucleotide can be achieved using a recombinant expression vector such as a chimeric virus or a colloidal dispersion system. Especially preferred for therapeutic delivery of antisense sequences, or hKCa3/KCNN3 polynucleotides, is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a hKCa3/KCNN3 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the hKCa3/KCNN3 polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Q2, PA317, and PA1 2, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for the therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 μm can encapsulate a substantial percentage of an aqueous buffer containing large macromolecules. RNA, DNA and intact virions can be encapsulated within the aqueous interior and be delivered to cells in a biologically active form (Fraley et al., 1981, *Trends Biochem. Sci*. 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., *Biotechniques* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

This invention involves administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan. By "subject" is meant any mammal, preferably a human.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science* 249:1527-1533, 1990, which is incorporated herein by reference.

The pharmaceutical compositions according to the invention may be administered locally or systemically. By "therapeutically effective dose" is meant the quantity of a compound according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman And Gilman's: The Pharmacological Bases of Therapeutics*, 8th ed., Pergamon Press, 1990; and *Remington's Pharmaceutical Sciences*, 17th ed., Mack Publishing Co., Easton, Pa., 1990, each of which is herein incorporated by reference.

Thus the identification of hKCa3/KCNN3 provides a useful tool for diagnosis, prognosis and therapeutic strategies associated with expression of hKCa3/KCNN3.

Trinuceotide Repeats

The hKCa3/KCNN3 gene is expressed in many neuronal tissues, and small conductance calcium activated potassium channels are known to play a vital role in regulating the firing pattern of neurons via the generation of afterhyperpolarizations (e.g., Nicoll, R. A., *Science* 241:545-5511, 1988). The hKCa3/KCNN3 gene has two trinucleotide arrays. Alterations in hKCa3/KCNN3 function from the expansion of the trinucleotide arrays might affect neural excitability and contribute to the pathophysiology of various neurological and neuropsychiatric disorders, such as schizophrenia and bipolar disease. The contribution of this locus to the age of onset of symptoms and clinical presentation may vary depending on the number of trinucleotide repeats and/or mutations in the hKCa3/KCNN3 alleles.

The trinucleotide arrays in the hKCa3/KCNN3 gene can be used to diagnose or determine the prognosis of a subject having or at risk of having a hKCa3/KCNN3-associated disorder by identifying the presence and determining the number of trinucleotide repeats (e.g., CAG/CTG) in the 5'-coding region of the hKCa3/KCNN3 gene. The number of trinucleotide repeats can be determined by methods well known to one of skill in the art (e.g., Speight, G., et al., *Am J. Med. Genet.* 74:204-206, 1997). The number of trinucleotide repeats in the subject can then be compared with the number of trinucleotide repeats in the hKCa3/KCNN3 gene in a normal (not affect by the hKCa3/KCNN3-associated disorder) subject or a control sample, such as a cell line. In order to determine the prognosis of an hKCa3/KCNN3-associated disorder, the number of trinucleotide repeats in the 5'-coding region of the hKCa3/KCNN3 gene from the subject can be compared to the number of trinucleotide repeats in the 5'-coding region of the hKCa3/KCNN3 gene from a series of control subjects having the hKCa3/KCNN3 disorder, wherein the prognosis for each control subject in the series is known.

Kits

The materials for use in the assay of the invention are ideally suited for the preparation of a kit. Such a kit may comprise a carrier means containing one or more container means such as vials, tubes, and the like, each of the container means comprising one of the separate elements to be used in the method. One of the container means may comprise a probe which is or can be detectably labeled. Such probe may be an antibody or nucleic acid sequence specific for hKCa3/KCNN3, or specific fragments thereof. For example, oligonucleotide probes of the present invention can be included in a kit and used for examining the presence of hKCa3/KCNN3 in a sample, as well as the quantitative (relative) degree of binding of the probe for determining the occurrence of specific strongly binding (hybridizing) sequences, thus indicating the likelihood for an subject having or predisposed to a disorder associated with hKCa3/KCNN3.

The kit may also contain a container comprising a reporter-means, such as a biotin-binding protein, such as avidin or streptavidin, bound to a reporter molecule, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the hKCa3/KCNN3 target sequence, this can be accomplished using oligonucleotide(s) that are primers for amplification. These oligonucleotide primers are based upon identification of the flanking regions contiguous with the target nucleotide sequence.

The kit may also contain a container containing antibodies which bind to hKCa3/KCNN3, or specific fragments thereof. Such antibodies can be used to distinguish the presence of hKCa3/KCNN3 or the level of expression of hKCa3/KCNN3 in a specimen. Where the kit utilizes antibodies to detect hKCa3/KCNN3, these antibodies may be directly labeled. The kit may also contain a container containing a reporter means, such as avidin or steptavin, bound to a reporter molecule such as an enzymatic, fluorescent, or radionucleotide label to identify the directly labeled antibody. Alternatively, the kit can utilizes antibodies that bind hKCa3/KCNN3 that are unlabeled. The kit may then also contain a container containing a second antibody which binds to the antibody specific for hKCa3/KCNN3. The second antibody can be directly labeled. The kit may also contain a container containing a reporter means, such as avidin or steptavin, bound to a reporter molecule such as an enzymatic, fluorescent, or radionucleotide label to identify the directly labeled second antibody.

Transgenic Animals

In another embodiment, the present invention relates to transgenic animals having cells that express hKCa3/KCNN3. Such transgenic animals represent a model system for the study of hKCa3/KCNN3 related disorders and the study of hKCa3/KCNN3 based therapeutics.

The term "animal" here denotes all mammalian species except human. It also includes an individual animal in all stages of development, including embryonic and fetal stages. Farm animals (pigs, goats, sheep, cows, horses, rabbits and the like), rodents (such as mice), and domestic pets (for example, cats and dogs) are included within the scope of the present invention.

A "transgenic" animal is any animal containing cells that bear genetic information received, directly or indirectly, by deliberate genetic manipulation at the subcellular level, such as by microinjection or infection with recombinant virus. "Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the present invention also contemplates the use of extrachromosomally replicating DNA sequences, such as might be engineered into yeast artificial chromosomes.

The term "transgenic animal" also includes a "germ cell line" transgenic animal. A germ cell line transgenic animal is a transgenic animal in which the genetic information has been taken up and incorporated into a germ line cell, therefore conferring the ability to transfer the information to offspring. If such offspring in fact possess some or all of that information, then they, too, are transgenic animals.

It is highly preferred that the transgenic animals of the present invention be produced by introducing into single cell embryos DNA encoding hKCa3/KCNN3, in a manner such that the polynucleotides are stably integrated into the DNA of germ line cells of the mature animal and inherited in normal Mendelian fashion. Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a preferred method, developing embryos are infected with a retrovirus containing the desired DNA, and transgenic animals produced from the infected embryo.

In a most preferred method the appropriate DNAs are coinjected into the pronucleus or cytoplasm of embryos, preferably at the single cell stage, and the embryos allowed to develop into mature transgenic animals. These techniques are well known. For instance, reviews of standard laboratory procedures for microinjection of heterologous DNAs into mammalian (mouse, pig, rabbit, sheep, goat, cow) fertilized ova include: Hogan et al., *Manipulating the Mouse Embryo*, Cold Spring Harbor Press, 1986; Krimpenfort et al., *Bio/Technology* 9:86, 1991; Palmiter et al., *Cell* 41:343, 1985; Kraemer et al., *Genetic Manipulation of the Early Mammalian Embryo*, Cold Spring Harbor Laboratory Press, 1985; Hammer et al., *Nature*, 315:680, 1985; Purcel et al., *Science*, 244:1281, 1986; Wagner et al., U.S. Pat. No. 5,175,385; Krimpenfort et al., U.S. Pat. No. 5,175,384, the respective contents of which are incorporated by reference.

The cDNA that encodes hKCa3/KCNN3 can be fused in proper reading frame under the transcriptional and translational control of a vector to produce a genetic construct that is then amplified, for example, by preparation in a bacterial vector, according to conventional methods. See, for example, the standard work: Sambrook et al., *Molecular Cloning: a Laboratory Manual*, Cold Spring Harbor Press, 1989, the contents of which are incorporated by reference. The amplified construct is thereafter excised from the vector and purified for use in producing transgenic animals.

The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or knocked out.

The transgene to be used in the practice of the subject invention is a DNA sequence comprising a modified hKCa3/KCNN3 coding sequence. In a preferred embodiment, the endogenous SKCa3 gene is disrupted by homologous targeting in embryonic stem cells. For example, the entire murine SKCa3 gene may be deleted. Optionally, the SKCa3 disruption or deletion may be accompanied by insertion of or replacement with other DNA sequences, such as a non-functional hKCa3/KCNN3 sequence. In other embodiments, the transgene comprises DNA antisense to the coding sequence for hKCa3/KCNN3. In another embodiment, the transgene comprises DNA encoding an antibody or receptor peptide sequence which is able to bind to hKCa3/KCNN3. Where appropriate, DNA sequences that encode proteins having hKCa3/KCNN3 activity but differ in nucleic acid sequence due to the degeneracy of the genetic code may also be used herein, as may truncated forms, allelic variants and interspecies homologues.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Gene Isolation Methods

A homology search was carried out for the human homolog of the newly discovered rat cDNA encoding a portion of the rSKCA3 channel (rat small conductance calcium-activated potassium channel, type 3) (accession # U69884). In a BLAST cDNA database search, the N-terminal regions of the rat cDNA encoding features of the channel not shared with other classes of potassium channels was used as a probe sequence. Such probes detected the 3' untranslated region of an anonymous cDNA sequence, AAD14 (accession # Y08263). Approximately 95% of the putative coding sequence of the human homolog was found. This sequence had 89% identity with the rat SKCa3 sequence (FIGS. 1 and 3). Identity is only 45% and 40%, respectively, with the SKCa1 (accession # U69883) and SKCA2 (accession # U69882) channels, suggesting that this is truly the homolog of the type 3 channel.

The human genomic database was surveyed for anonymous sequence tagged sites (STSs) for homology with the AAD14 cDNA sequence. It identified a clone, STS-G16005, that aligns with nucleotides 328-940 of the cDNA. This region of the cDNA encodes not only the first 128 bp of the hKCa3/KCNN3 sequence as one ORF, but it also encodes the anonymous ORF that AAD14 was originally reported to contain. That original ORF has two polyglutamine stretches encoded by perfect CAG repeats (12 and 14 in length). The two ORFs contained on this genomic and cDNA sequence are out of frame and separated by a single stop codon. Removing one nucleotide eliminates the stop codon and joins both ORFs into a single ORF within the same exon.

To test this idea, the region was sequenced multiple times (n=6) in normal human genomic DNA. Rather than the reported string of eight Cs (position 632-640 in FIG. 1), seven were repeatedly identified. Deletion of this additional C from the AAD14 sequence put the two ORFs in-frame (FIG. 2, AAD 14 Fr. 1). This indicates that the authentic initiator methionine for hKCa3/KCNN3 resides at least 800 bp farther upstream than that published for the rat homolog (Kohler, M., et al., Science 273:1709-1714, 1996), and the hKCa3/KCNN3 protein contains two polyglutamine stretches in its N-terminus.

This region from normal human genomic DNA was amplified using the polymerase chain reaction (PCR). By sequencing the relevant fragments it was confirmed that the ORF containing the polyglutamines was transcribed from a single exon, and were able to demonstrate the first and second CAG arrays were polymorphic. The primers used for PCR are described below and have utility for diagnosis. Comparison of the AAD 14 cDNA sequence with that of the genomic fragment of hKCa3/KCNN3 and STS-G16005 also demonstrated polymorphism of the two CAG arrays. The second polyglutamine repeat is 14 residues long in AAD14 but 19 residues long in both genomic sequences; the first polyglutamine repeat is two residues longer in AAD14 and STS-G16005 than the genomic sequence of hKCa3/KCNN3.

Figure 4:
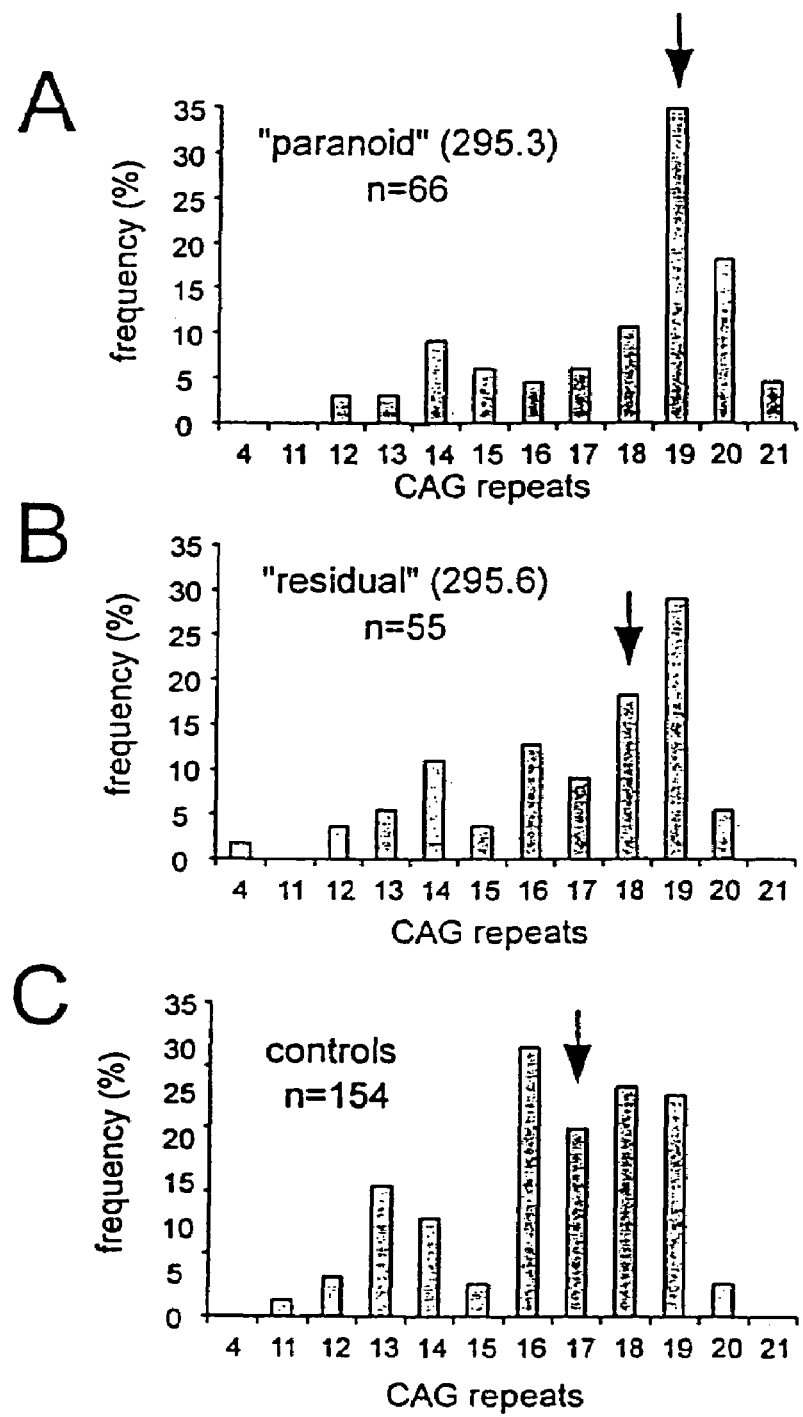
FIGS. 4A-C is a series of graphs illustrating the distribution of CAG repeat lengths for the shorter allele of schizophrenia patients related to diagnosis.

Comparison of the translated protein sequences of hKCa3/KCNN3 and its rat homologue (rSKCa3) shows 14 amino acid differences in the first 278 residues of the published rat sequence, many of them being conservative substitutions (FIGS. 2 and 4). The presence of two additional thymidines in the AAD14 nucleotide sequence compared to that of its rat homologue and the hKCa3/KCNN3 sequence (FIGS. 1 and 3) introduces an apparent premature stop codon in the AAD14 ORF; these extra Ts are located within polypyrimidine tracts and most likely represent sequencing errors. This notion is reinforced by the hKCa3/KCNN3 sequence data and observing that translation of the remaining 313 base pairs of the AAD14 sequence reveals a second ORF that is again identical to the rat SKCa3 sequence, with one conservative substitution at 291 (FIGS. 2 and 4). To test this idea, this region from normal human brain cDNA was amplified and the relevant region sequenced. As shown in FIG. 3, the additional T's are not present in the sequence. Removal of these additional nucleotides puts the known coding region in the AAD14 cDNA in one reading frame (FIGS. 2 and 4). These two adjacent ORFs reflect the single ORF encoded in the hKCa3/KCNN3 channel.

The AAD14 cDNA is an incomplete sequence and does not contain the initiator methionine or the last 0.5 kb at the 3'-end. PCR was therefore used to isolate an overlapping hKCa3/KCNN3 fragment from human brain cDNA (Marathon cDNA, Clontech) that contained the entire 3'-end of the coding region by PCR (FIGS. 1 and 3). The human and rat genes show a high degree of conservation in this region (FIGS. 3 and 4). The isolation of three hKCa3/KCNN3 clones from human lymphocytes (accession numbers Y08263, AA284005; AA285078) suggests that this gene might encode one of the lymphocytic SKCa channels that have been reported to play an important modulatory role in calcium signaling involved in mitogen-induced activation.

Example 2

Expression in vitro

In a further construct, the 3' end of the hKCa3/KCNN3 gene was spliced into the AAD 14 cDNA at a unique SphI site. A methionine was placed at the 5'-end of the coding region and the clone was placed under control of the SP6 promoter. A cRNA from this construct or from the DNA sequence corresponding to this construct was expressed in mammalian cells in order to characterize the biophysical and pharmacological properties of the channel. This construct, when expressed in mammalian cell lines or amphibian oocytes, serves as an extremely valuable tool for high-throughput screening studies to identify hKCa3/KCNN3-specific modulating agents; or agents that specifically alter other channels whose activity is a function of hKCa3/KCNN3 activity, such compounds might have therapeutic value for the treatment of schizophrenia, bipolar disorder, or other neuropsychiatric disorders. Since hKCa3/KCNN3 was initially isolated from lymphocytes, it might encode the small conductance calcium-activated potassium channels in these cells that play an important role in mitogen-induced activation; hKCa3/KCNN3-blockers might therefore be useful as immunosuppressive agents.

Example 3

Diagnostic Test Methods

Pairs of PCR primers (listed below in table) were designed to that would allow amplification from genomic DNA the region of the hKCa3/KCNN3 gene flanking the CAG repeats. These primer pairs were used sequentially. First the two unlabeled primers, 22QA and 22QB were used, and the resultant products were cloned into the TA cloning vector (PCRII, Invitrogen) and manually sequenced using as sequencing primers oligonucleotides based on vector sequence. This sequencing confirmed that both CAG repeats were polymorphic in the population.

For example, these PCR products, or nested PCR products produced by primers directed to the internal sequence, could be formed using either fluorescent-labeled primers or fluorescent nucleotides to form products of this reaction that could be run on an acrylamide gel in an automated sequence analysis system with fluorescence detection (Pharmacia) to resolve the size of the PCR product. This would reflect the number of the CAG repeats in the gene.

TABLE 1

PCR Primers

| Primer | Length | Start | End | Sequence | Notes |
|---|---|---|---|---|---|
| 22QA | 23 | 339 | 361 | ACCCCAAGTGCCCCTGTCCATCC (SEQ ID NO:10) | Upstream of repeats |
| 22QB | 24 | 782 | 805 | ATCTCCGTGAAGGGGTTGCTGTCC (SEQ ID NO:11) | Between stop codon and SK3 ATG |
| 22QC | 24 | 589 | 612 | CTGAAAGCGGTGGGAGAGGAGTGC (SEQ ID NO:12) | Make 274 bp PCR product with QA3 |
| 22QD | 26 | 414 | 439 | CACCGTCAGTGTCACCAGTAGTCCC (SEQ ID NO:13) | For sequencing of stop codon region |

NB: positions indicated on the Y08263 DNA (=AAD14)

PCR Reactions

Reagents:
Taq Polymerase Buffer 10X (Gibco)
50 Mm $Mg^{2+}$ (Gibco)
Taq Polymerase 5U/µl(Gibco)
dNTPs mix 10 mMach (Gibco)
DNA human genomic 1 µg/µl
primer 22QA 100 ng/µl
primer 22QB 100 ng/µl Reactions:
5 µl Taq Pol Buffer 10X
1.5 µl $Mg^{2+}$ 50 mM
1 µl dNTPs 10 mM
5 µl primer 22QA
5 µl primer 22QB
31.5 µl $H_2O$
1 µl genomic DNA (or positive control DNA)
50 µfinal volume
+0.25 µl Taq Polymerase 5U/µl

| Cycling conditions: | | |
|---|---|---|
| 1 cycle | 3 min | 94° C. |
| 40 cycles | 30 sec | 94° C. |
| | 30 sec | 65° C. |
| | 1 min | 72° C. |

10-15 µof each reaction is analyzed on a 2% agarose gel in 1×TAE.

Example 4

Association Between Length of CAG Repeats and Schizophrenia

The human KCa3 gene contains two adjacent polyglutamine repeat arrays in its N-terminal region (Chandy, K. G., et al., *Molec. Psych.* 3:32-37, 1998, herein incorporated by reference); this feature has been subsequently recognized in the rat gene as well (GenBank accession numbers AF031815, U69884). Interestingly, the two polyglutamine arrays are linked by a proline-rich region containing the motif PXXP repeated five times, and this segment may be targeted by signaling molecules possessing SH3 domains (Kuriyan, J., and Cowburn, D., *Annu. Rev. Biophys. Biomol. Struct.* 26:259-288, 1997). The second polyglutamine repeat is highly polymorphic in Caucasian European and North American populations, ranging from 10-28 repeats in length, with a modal value of 19 repeats (Chandy et al., 1998, supra;

Bowen, T., et al., *Mol. Psych.* 3:32-37, 1998, herein incorporated by reference). Case-control analyses have recently shown a significant over-representation of longer hKCa3/KCAN3 CAG-repeat alleles in Caucasian schizophrenia patients compared with ethnically matched controls (see Example 8).

1. Materials and Methods

Subjects: This study was performed after approval by the local Ethics Committee, and all subjects provided informed consent permitting use of their DNA for research. One hundred sixty five Jewish schizophrenic patients meeting DMS-IV criteria for schizophrenia (24) were recruited among patients hospitalized in Abarbanel Mental Health Center, Bat-Yam, Israel. Diagnoses were made during hospitalization by structured interviews, and confirmed in clinical interviews during the study period by a consensus of at least two board certified psychiatrists. Diagnoses were established prior to the genetic study, and patients were not included if there was any disagreement in diagnosis. Israeli controls were recruited from our anonymous "DNA bank" obtained from 154 healthy Jewish individuals at least 20 years of age who had no history of psychiatric disease.

Statistical analysis. The Wilcoxon Rank-Sum test with tied midranks (Lehmann, E. L., *Nonparametrics: statistical methods based on ranks*, McGraw-Hill, New York, 1975) was used to compare pairs of frequency distributions. For comparison of multiple distributions the Kruskal-Wallis test (Lehmann, ,1975, supra) was used. Testing for correlation was done by the t-test (Armitage, P., and Berry, G., *Statistical Methods in Medical Research*, 2nd Ed., Blackwell Scientific Publications, Oxford, 1987). Computer programs to carry out these tests were kindly provided by Dr. Howard Tucker (Department of Mathematics, University of California, Irvine). The Fisher Exact test on dichotomized data was carried out using the IRFIS program (GG), and the 95% confidence interval on the odds ratio calculated according to Woolf (Woolf, B., *Ann. Hum. Genet.* 19:251-253,1955).

Allele sizing. Genomic DNA was prepared from 10 ml of peripheral blood (Miller, S. A., et al., *Nucl. Acid. Res.* 16: 1215, 1988). DNAs were amplified by PCR using the following primers:

```
forward   5' GCAGCCCCTGGGACCCTCGCT 3'       (SEQ ID NO:14)

reverse   5' ACATGTAGCTGTGGAACTTGGAGAGT 3'  (SEQ ID NO:15)
```

The expected product size is about 300 bp, and depends on the number of CAG repeats in the polymorphic 3' most of the two clusters in the N-terminal region of hKCa3/KCNN3/KCNN3. $^{32}$P-dCTP in was used in the reaction mixture in a total volume of 15 µl, and DMSO (final 10%) was added to inhibit nonspecific amplification products. Conditions of PCR were 30 cycles at 94° C. for 30 seconds, 65° C. for 30 seconds, 72° C. for 45 seconds, following initial denaturation at 94° C. for 3 min.

The PCR products were diluted in formamide loading buffer, denatured at 70° C. for 10 min and loaded onto a denaturing sequencing gel. The PCR product- sizes were determined by comparison with an M13 sequencing ladder and internal controls consisting of three cloned and sequenced alleles of known repeat length (Chandy, K. G., et al., *Molec. Psych.* 3:32-37, 1998). The trinucleotide repeats often do not appear as single discrete DNA bands on polyacrylamide gel, but rather as one major band accompanied by one or more stutter bands owing to PCR artifacts; in such cases the strongest band for each allelic form was used for the determination. The presence of a single band was scored as a homozygous allele. All genotyping was carried out in a blinded fashion with control and patient samples randomly mixed together. The length assignment of several samples was independently confirmed.

2. Association Between Length of CAG Repeats and Schizophrenia in Israeli Jews

The number of CAG repeats in the second CAG region of the hKCa3/KCNN3/KCNN3 gene was analyzed in 165 Israeli Jewish schizophrenia patients and in 154 unaffected Jewish controls. FIG. 1A shows the frequency of alleles with different CAG repeat lengths for all patients with schizophrenia and unaffected controls. This repeat is highly polymorphic in both populations, with an overall range of alleles from 4 to 25 CAGs. The modal allele for the control group is 18 CAG repeats, unlike the modal allele of 19 repeats reported in European and North American Caucasians (see Example 8). The modal allele for Israeli Jewish patients with schizophrenia is 19 CAG repeats, and the 3 longest alleles (23-25 repeats) are uniquely represented among patients. Using the Wilcoxon Rank Sum test it was found that the distributions of alleles are significantly different between patients and controls ($p<10^{-6}$). Dichotomizing the sample at the overall modal allele of 19 CAG repeats (Chandy et al., 1998, supra), and applying the Fisher Exact test, also shows a highly significant excess of longer alleles in patients compared with controls ($p<10^{-6}$, odds ratio (OR)=4.9, 95% confidence interval (CI)=3.1-7.8).

This association was further analyzed by separately comparing CAG repeat lengths in 84 Ashkenazi Jewish patients with 102 ethnically matched controls, and 75 Sephardic Jewish schizophrenia patients with 39 controls; subjects whose parents were of mixed ethnic origins were excluded from this analysis. The distribution of alleles is significantly different between Askenazi schizophrenia patients and controls using the Wilcoxon test (FIG. 3B, $p=1.7\times10^{-4}$). A similar analysis reveals a significant difference between Sephardic Jewish schizophrenia patients and ethnically matched controls (FIG. 3C; $p<10^{-6}$). Dichotomization of the sample at the modal allele (19 repeats) and analysis by the Fisher Exact test revealed a significant excess of longer alleles in both Sephardic and Ashkenazi schizophrenia patients compared with ethnically matched controls (Sephardim, $p<10^{-6}$, OR=13, 95% CI 4.1-45; Ashkenazim, $p=2.9\times10^{-5}$, OR=3.2, 95% CI 1.8-5.6). Thus, the differences between patients and controls in these Jewish populations are far more robust than those found in more heterogeneous European and North American Caucasian populations (Chandy et al., 1998, supra; and Example 8).

3. Association Between Length of CAG Repeats and Schizophrenia in males and Females.

The population was separately analyzed according to sex (data not shown). A comparison of female schizophrenia patients (n=67) with female controls (n=108), showed a highly significant excess of longer alleles in patients ($p<10^{-6}$ by Wilcoxon and Fisher Exact). A similar comparison of 98 male patients and 46 male controls also revealed a highly significant difference between patients and controls, ($p<10^{-6}$ by Wilcoxon and Fisher Exact). There was no significant difference between the allele distributions of males versus females, among patients or controls, using either the Wilcoxon or Fisher Exact tests.

4. Both Alleles are Associated with Schizophrenia.

The allele distributions shown in FIGS. 3A-C include both alleles from each individual. To determine if only one or both alleles in any individual contribute to disease risk, the allele distributions of the longer (FIG. 3D) and shorter (FIG. 3E) alleles were separately compared in each of 165 schizophrenia patients and 154 unaffected controls. Both the shorter and the longer alleles from each subject were significantly longer in schizophrenia patients than controls, using either the Wilcoxon test ($p=1.6 \times 10^{-5}$ for the shorter; $p<10^{-6}$ for the longer) or the Fisher Exact test on dichotomized data ($p<10^{-6}$ for both; OR=3.31, 95% CI=2.1-5.5 for the shorter allele; OR=5.36, 95% CI=3.1-9.2 for the longer allele). The distributions of the sum of the two alleles (data not shown) were also significantly longer in schizophrenia patients compared with controls (Wilcoxon, $p<10^{-6}$, Fisher Exact $p<10^{-6}$, OR=4.5, 95% CI=2.4-8.5). When the Sephardim and Askhenazi populations are considered separately, the long allele makes a greater contribution to disease susceptibility in Sephardim (Fisher Exact: $p<10^{-6}$, OR=19, 95% CI 4.3-85.6) than in Ashkenazim (Fisher Exact: $p=8.2 \times 10^{-5}$, OR=3.6, 95% CI 1.9-7.0). Likewise, while the overall contribution to disease risk is less for the shorter of two alleles than the longer, its contribution is greater in Sephardim (Fisher Exact: $p=0.0076$, OR=9.5, 95% CI=1.2-75) than in Ashkenazim (Fisher Exact: $p=0.047$, OR=4.5, 95% CI=0.9-22).

5. Type of Schizophrenia, Disease Severity and CAG Repeat Length.

Several types of schizophrenia are recognized based on differences in clinical features, prognosis and response to medication. The genetic factors that enhance disease susceptibility of each of these forms of schizophrenia may differ, and it is therefore possible that the CAG repeat length in the hKCa3/KCNN3 gene may vary with diagnosis. The patient pool used in the above studies included substantial representation within only four of these categories, namely those with DSM-IV diagnoses 295.1 ("disorganized"), 295.3 ("paranoid"), 295.6 ("residual") and 295.7 ("schizoaffective disorder"). The Kruskal-Wallis test was applied to this group of four allele distributions (Table 2) which revealed a statistically significant difference between them ($p=0.021$). Carrying out separate comparison for the longer and shorter allele in each patient indicated that the distributions for the longer alleles were not significantly different from one another ($p=0.60$). On the other hand, the distributions of the shorter alleles (Table 3) were significantly different ($p=0.027$). Pairwise comparisons (Wilcoxon test) showed statistically significant differences between "paranoid" and "residual," the two largest groups among our patient population ($p=0.005$), as well as between the "paranoid" and "schizoaffective disorder" groups ($p=0.025$). No other pairwise comparison within this table yielded a significant difference.

TABLE 2[a]

| CAGs, | DSM-IV Diagnosis: | | | | |
|---|---|---|---|---|---|
| all alleles: | 295.1 | 295.3 | 295.6 | 295.7 | totals |
| 4 | 0 | 0 | 1 | 0 | 1 |
| 13 | 1 | 3 | 3 | 0 | 7 |
| 14 | 0 | 2 | 3 | 2 | 7 |
| 15 | 2 | 6 | 6 | 2 | 16 |
| 16 | 4 | 4 | 3 | 2 | 13 |
| 17 | 2 | 5 | 7 | 1 | 15 |
| 18 | 5 | 11 | 14 | 2 | 32 |
| 19 | 14 | 27 | 30 | 7 | 78 |
| 20 | 16 | 45 | 30 | 6 | 97 |
| 21 | 7 | 21 | 11 | 1 | 40 |
| 22 | 2 | 6 | 0 | 1 | 9 |
| 23 | 0 | 1 | 1 | 0 | 2 |
| 24 | 1 | 0 | 1 | 0 | 2 |
| 25 | 0 | 1 | 0 | 0 | 1 |
| | 54 | 132 | 110 | 24 | 320 |

[a]Distribution of lengths of CAG repeats in hKCa3/KCNN3 of patients (all alleles) grouped according to their DSM-IV diagnosis. There is a significant difference between these distributions (overall $p = 0.021$ by the Kruskal-Wallis test).

TABLE 3[a]

| CAGs, | DSM-IV Diagnosis | | | | |
|---|---|---|---|---|---|
| shorter allele: | 295.1 | 295.3 | 295.6 | 295.7 | totals |
| 4 | 0 | 0 | 1 | 0 | 1 |
| 12 | 1 | 2 | 2 | 0 | 5 |
| 13 | 0 | 2 | 3 | 2 | 7 |
| 14 | 1 | 6 | 6 | 2 | 15 |
| 15 | 4 | 4 | 2 | 1 | 11 |
| 16 | 2 | 3 | 7 | 1 | 13 |
| 17 | 1 | 4 | 5 | 0 | 10 |
| 18 | 5 | 7 | 10 | 3 | 25 |
| 19 | 7 | 23 | 16 | 2 | 48 |
| 20 | 5 | 12 | 3 | 1 | 21 |
| 21 | 1 | 3 | 0 | 0 | 4 |
| | 27 | 66 | 55 | 12 | 160 |

[a]Distribution of lengths of CAG repeats in hKCa3/KCNN3 of patients (shorter allele only) grouped according to their DSM-IV diagnosis. There is a significant overall difference between these distributions ($p = 0.027$ by the Kruskal-Wallis test). Pairwise comparisons using the Wilcoxon test showed a significant difference between the distributions of subjects with diagnoses of 295.3 ("paranoid" type) and 295.6("residual" type; $p = 0.0049$), and between 295.3 and 295.7 ("schizoaffective disorder"; $p = 0.025$).

This diagnosis-related difference between the shorter alleles in schizophrenia patients is graphically illustrated in FIG. 4. The distributions for those patients diagnosed with "paranoid" (DSM-IV 295.3) and "residual" (DSM-IV 295.6) types of disease, the two most frequent diagnosis among the subjects (FIG. 4A and FIG. 4B) are displayed together with that of the shorter alleles of the unaffected controls (FIG. 5C). The shift in the median values of these distributions (indicated by arrows) is evident. The Wilcoxon test on pairwise comparisons showed a significant difference between the distributions in panels A and B ($p=0.0049$), and between panels A and C ($p=2.1 \times 10^{-6}$).

The relationship between length of CAG repeats (using all alleles) and the severity of disease as measured by the total number of recorded hospitalizations was also determined. Examining the distributions shown in Table 4 by the Kruskal-Wallis test revealed no significant association ($p=0.78$). Lastly, the relationship between CAG repeat length and age at first hospitalization, a measure of the age-of-onset of disease, was determined. A very weak but statistically significant positive correlation (i.e., between longer alleles and later age of onset) was found by a two-tailed t-test for all alleles ($p=0.0025$, $r=0.17$), as well as for the longer allele (p=0.024, r=0.17) and the shorter allele (p=0.0047, r=0.22) in each patient analyzed separately.

In this study, a striking difference was found in the CAG repeat length in the hKCa3/KCNN3/KCNN3 gene between Israeli Jewish patients with schizophrenia and ethnically matched controls. Both alleles in an individual contribute to disease risk, and patients diagnosed with "paranoid" or "disorganized" types of schizophrenia appear to have longer repeats than patients with other forms of this disease. This difference is evident both in Ashkenazi and Sephardic Jews, as well as in males and females. The magnitude and statistical significance of these differences is substantially greater than those obtained in previously reported studies on Caucasian populations from France, the United Kingdom, Ireland and North America (Example 8 and Chandy et al., 1998, supra). This may be the result of a higher degree of genetic homogeneity within these Jewish populations (Karlin, S., et al., *Am. J. Hum. Genet.* 31:341-365, 1979), and there are distinct and well-established advantages to studying a more homogeneous population when confronted with the inherent complexity of identifying alleles of small effect in a polygenic disorder. Decreasing the population variance at other contributing loci may highlight the effect produced by the locus under investigation.

TABLE 4[a]

| | Number of hospitalizations: | | | |
|---|---|---|---|---|
| #CAGs: | 1-4 | 5-9 | >9 | totals |
| 4 | 0 | 1 | 0 | 1 |
| 12 | 3 | 0 | 2 | 5 |
| 13 | 5 | 4 | 0 | 9 |
| 14 | 4 | 8 | 3 | 15 |
| 15 | 4 | 3 | 5 | 12 |
| 16 | 8 | 2 | 7 | 17 |
| 17 | 5 | 6 | 2 | 13 |
| 18 | 13 | 15 | 19 | 47 |
| 19 | 45 | 33 | 26 | 104 |
| 20 | 26 | 27 | 19 | 72 |
| 21 | 7 | 11 | 5 | 23 |
| 22 | 1 | 1 | 3 | 5 |
| 23 | 1 | 0 | 1 | 2 |
| 24 | 2 | 0 | 0 | 2 |
| 25 | 0 | 1 | 0 | 1 |
| | 124 | 112 | 92 | 328 |

[a]Distribution of lengths of CAG repeats in hKCa3/KCNN3 of patients (all alleles) grouped according to the total number of hospitalizations. There is no significant difference between these distributions (p = 0.48 by the Kruskal-Wallis test).

Example 5

Expression of hKCa3/KCNN3/KCNN3 Transcripts in Human Tissues

1. Materials and Methods

Northern blot and in situ analysis: Northern blots of RNA from human tissues (multiple organs, lymphoid tissues, regions of brain and established cell lines) were obtained from Clontech (Palo Alto, Calif.), hybridized with a hKCa3/KCNN3-specific probe (~500 bp ApaI fragment, nucleotides 330-825 of the 5' coding region), and washed at a final stringency of 0.1×SSC, 0.1% SDS for 30-40 min. at 55° C. All blots were exposed at −80° C. with an intensifying screen for 15 days.

Histological material came from the brains of two normal adults with no history of drug abuse or neurological illness and no evident Alzheimer's pathology. Blocks of the upper brainstem and basal ganglia were cut from fresh-frozen coronal slabs of each brain (Jones, E. G., et al., *J. Neurosci. Methods* 44: 133-44, 1992). For in situ hybridization, each block was raised to 4° C. over 20 minutes, fixed in cold 4% paraformaldehyde in 0.1 M phosphate buffer for ~24 hours at 4° C., then infiltrated with 30% sucrose, re-frozen in dry ice, and sectioned serially in the frontal plane on a freezing microtome at 40 μm. Free-floating sections were hybridized with 1×10$^6$ cpm/μl of ($\alpha$-$^{32}$P-UTP)-labeled, anti-sense (or sense) riboprobes transcribed from a linearized cDNA template, using a previously described protocol (Akbarian, S., et al., *Cerebral Cortex* 5:550-6, 1995). cRNA probe concentration and specific activity were approximately the same in all in situ runs. Sense controls gave weak background labeling only, comparable to that seen over the white matter. After hybridization, the sections were exposed to β-Max autoradiographic film (Amersham, Arlington Heights, Ill.) for 10-14 days. After film development, slides were dipped in Kodak NTB2 photographic emulsion, exposed at 4° C. for 6 weeks, developed in Kodak D19 developer, fixed with Kodak Rapid Fix and counter-stained with cresyl violet.

2. Results.

The findings of Example 6 above demonstrate a strong association between the CAG repeat length and the development of schizophrenia in Israeli Jews. An understanding of the mechanisms by which CAG repeats in hKCa3lKCAN3/KCMN3 might affect the risk of developing schizophrenia requires knowledge of where this gene is expressed within human tissues, and how its distribution might relate to disease symptoms. Thus Northern blot and in situ-hybridization studies were used to probe diverse human tissues with an hKCa3/KCAN3/KCNN3-specific DNA fragment.

Among a variety of human tissues examined, Northern blot analysis revealed expression to be largely limited to brain, striated muscle and lymphoid tissues. Two predominant transcripts (~9 and ~13 kb) were found in human brain, heart and skeletal muscle, and in lymph-node and spleen; some smaller mRNA species were also visible, for example in skeletal muscle and spleen. Interestingly, several ESTs encoding hKCa3/KCNN3 have been isolated from human lymphocytes (accession numbers AA491238, Y08263, AA285078, AA284005), and the human T-cell line Jurkat expresses a $K_{Ca}$ channel with pore properties similar to those of hKCa3/KCNN3 (Grissmer, S., et al., *J. Gen. Physiology* 99:63-84; Grissmer, S., et al., *J. Gen. Physiology* 102:601-630, 1993). Screening a panel of transformed cell lines revealed abundant expression of a ~2.5 kb hKCa3/KCAN3 transcript in the Rajii B-cell line and the erythroleukemic cell K562; fainter transcripts of varying sizes were seen in other cell lines (HL-60: promyelocytic leukemia; HeLa (S3): epithelial carcinoma; MOLT-4: lymphoblastic leukemia; SW480: colorectal adenocarcinoma; A549: lung carcinoma; G361: malignant melanoma.

Within the brain, a relatively high intensity of hKCa3/KCNN3 mRNA was detected in the human substantia nigra, basal ganglia, and subthalamic nuclei. The human hippocampus 3 and amygdala, two regions previously implicated in affect and psychosis (Moghaddam, B., et al., *J. Neurosci.* 17:2921-2927, 1997; Hirsch, S. R., et al., *Pharmacol., Biochem. Behav.* 56:797-802, 1997), also show abundant expression of hKCa3/KCNN3. Only lower levels of hKCa3/KCNN3 expression are seen in the cerebral cortex, cerebellum and thalamus.

Consistent with these findings, in situ hybridization studies on sections of human midbrain more precisely localized hKCa3/KCNN3 transcripts to the human substantia nigra and ventral tegmental area hKCa3/KCNN3 mRNA was also found in the putamen, but not in the red nucleus, cerebral peduncle or globus pallidus. This distribution is consistent with hKCa3/KCNN3 being expressed in dopaminergic neurons of the nigrostriatal and mesolimbic pathways that have previously been implicated in schizophrenia (Haber, S. N., and Fudge, J. L., *Schiz. Bull.*, 23:471-482, 1997). The dopamine $D_2$ receptor is also primarily localized in these pathways, and the affinity of antipsychotic drugs for this specific isoform of the dopamine receptor appears to correlate with their clinical potency (Seeman, P., and Tallerico, T., *Mol. Psych.*, 3:123-134, 1998).

3. Discussion

A theory put forward by Perutz et al. (Perutz, M. F., et al., *Proc. Natl. Acad. Sci. USA*, 91:5355-5358 35-37, 1994) regarding expanded CAG repeats contribute to the pathogenesis of schizophrenia, suggests that polyglutamine repeats behave as polar zippers, and that proteins begin to oligomerize once the repeat length progresses beyond a critical threshold of 35 to 40 repeats. Does the hKCa3/KCNN3 channel fit Perutz's "rule of 35"? Functional potassium channels are tetramers, and the N- and C-termini are located within the cytoplasm (Ishii, T. M., et al., *Proc. Natl. Acad. Sci. USA* 94:11651-1165, 1997; Spencer, R. H., et al., *J. Biol. Chem.* 27:,2389-239, 1997). If each hKCa3/KCNN3 monomer contained the modal number of glutamines in the second repeat (i.e., 18 repeats), the tetramer would contain 72 glutamines from this region. An additional 48 glutamines would be contributed by the first repeat (12 per monomer) and another 20 by the short polyglutamine stretch in the C-terminus (5 per monomer). Such an hKCa3/KCNN3 tetramer would therefore display 140 glutamines contained within repeats on its cytoplasmic surface, which is greater than that of the longest allele seen in Huntington's disease (121 repeats). Since $K_{Ca}$ channels are able to form heteromultimers as well as homomultimers (Ishii et al., 1997, supra), hKCa3/KCNN3 proteins with short and long polyglutamine repeats are likely to co-assemble. An individual carrying two different hKCa3/KCNN3 alleles would have a diversity of expressed channels, including two kinds of homotetramers, and various heterotetramers with differing combinations of long- and short-repeat subunits. In addition, heteromultimers formed from combinations of hKCa3/KCNN3 and other members of the family, will provide another level of heterogeneity in channel phenotype. If each of these channels has distinct biophysical properties, regulation of the cell's membrane potential will be determined by the behavior of a complex ensemble of hKCa3/KCNN3 channels.

Since hKCa3/KCNN3 channels are expressed in restricted regions of the brain, it is easy to envision a pathogenic mechanism involving subtle alterations in channel function (and therefore neuronal membrane potential) produced by tetrameric channels containing a larger number of polyglutamines. Alterations in membrane potential (and therefore neuronal behavior) might occur once a critical "threshold" has been crossed. Thus, both alleles of an individual contribute to the formation of functional $K_{Ca}$ channels and would therefore be expected to be associated with disease. This expectation is consistent with our finding of a shift toward longer repeats for both alleles in individuals with schizophrenia (FIGS. 1D and E).

Expanded CAG alleles are generally dominant in those neurodegenerative diseases in which they have been implicated, and the phenotype they produce is qualitatively different from that of null alleles; the pathogenicity of such expanded polyglutamine repeats is therefore thought to be the result of a novel "gain-of-function." If longer polyglutamine repeats in hKCa3/KCNN3 enhance channel function in a graded manner, one might expect the membrane potential of neurons expressing these channels to be excessively hyperpolarized, leading to a progressive lengthening in the inter-spike interval and an alteration of neuronal excitability. If this is true, one might expect to see a relationship between CAG repeat length and some manifestation of disease phenotype. Two of the findings provide at least some support for this expectation. First, we observe a relationship between the length of CAG repeats and the type of schizophrenia exhibited is observed; greater length of the shorter allele in affected individuals is associated with the "paranoid" and "disorganized" types of schizophrenia, compared with the "residual" and "schizoaffective disorder" forms of disease (Table 3, FIG. 2). Additionally, we find a very weak correlation between allele length and the age at first hospitalization, although no significant relationship between allele length and the number of hospitalizations (Table 4). The weakness of such associations may reflect at least in part the relative insensitivity of our current measures of disease severity (Johnson, J. E., et al., *Am. J. Med Genetics* 74:275-80, 1997), as well as a degree of subjectivity involved in establishing the different types of diagnoses (*Diagnostic and statistical manual of mental disorders*: DSM-IV, 4th ed., American Psychiatric Association, Washington D.C., 1994).

Which neuronal pathways in the brain could be modulated by hKCa3/KCNN3 channels and contribute to the pathophysiology of schizophrenia? Although SKCa and $IK_{Ca}$ channels are structurally and functionally similar, they each have distinct patterns of tissue expression. In the rat brain, KCa3 has the narrowest regional expression in the family, with KCa2 being widely expressed, and KCa4 not being expressed in neuronal tissue. The observations of these experiments on the distribution of hKCa3/KCNN3 in the human brain are consistent with the major findings in the rat (Köhler, M., et al., *Science* 273:1709-1714, 1996). The relative intensity of hKCa3/KCNN3 expression in the human substantia nigra, ventral tegmental area, basal ganglia, subthalamic nuclei, amygdala and hippocampus suggests a role for this channel in two of the four major dopaminergic pathways in the human brain, pathways that have been implicated in schizophrenia. The nigrostriatal pathway connects the substantia nigra to the caudate and putamen while the mesolimbic pathway connects the ventral tegmental area to the amygdala and hippocampus. Defects in these dopaminergic pathways are thought to contribute to the pathophysiology of schizophrenia, and to the psychomotor disorders characteristically associated with the disease. It is of note that these two pathways encompass the very limited region of the CNS that expresses dopamine $D_2$ receptors, and that the clinical potency of antipsychotic drugs appears to correlate with their affinity for this specific isoform of the dopamine receptor. The human hippocampus and amygdala are two regions also previously implicated in affect and psychosis (Moghaddam, B., et al., *J. Neurosci.* 17: 2921-2927, 1997; Hirsch, S. R., et al., *Pharmacol., Biochem. Behav.* 56:797-802, 1997); in vivo and postmortem imaging studies of schizophrenia patients have repeatedly shown a reduction in the volume of the arnygdala and hippocampus compared with controls. Only low levels of hKCa3/KCNN3 expression are seen in the cerebral cortex, cerebellum and thalamus, regions that receive inputs from the tegmentum and include the third major dopaminergic pathway (mesocortical) implicated in schizophrenia.

Since schizophrenia is a polygenic disease and is thought involve 5-10 different genes (Karayiorgou, M., and Gogos, J. A., Neuron 19:967-79, 1997), it is clearly important to determine the contribution of hKCa3/KCNN3 to disease risk, one measure of which is the odds ratio. The odds ratio for the allelic association of hKCa3/KCNN3 and schizophrenia from dichotomized data is substantial, both in Sephardim (OR=13 for all alleles, OR=19 for longer allele only) and Ashkenazim (OR=5.0 for all alleles, OR=3.6 for longer allele). These values are significantly greater than those observed in earlier studies with more heterogeneous European and North American Caucasians (OR=2.4, Chandy et al. (1998, supra); OR=1.4, Bowen et al. (1998, supra), suggesting that hKCa3/KCNN3 is a more important risk factor for schizophrenia among Israeli Jews, and more so among Sephardic than Ashkenazi Jews.

Example 6

Association Between a Polymorphic CAG Repeat in the hKCa3/KCNN3 Gene and Schizophrenia In a further investigation, 194 patients meeting DSM-III-R criteria for schizophrenia and 183 controls matched for age and sex were studied (Bowen et al., Mol. Psychiatry 3:266-269, 1998, herein incorporated by reference). All of the patients were Caucasians born in the UK or Eire. The patients included single affected individuals from 129 families containing two or more cases of schizophrenia. The remaining 65 subjects were recruited from inpatient and day hospitals in South Wales. The patient group consisted of 135 males and 59 females, mean age of 45 years (s.d. 13). Diagnoses were made using OPCRIT version 3.31 using all available data including a semistructured interview and case notes. Age-at-onset was defined as age at first psychiatric contact. Controls consisted of 123 males and 60 females with a mean age of 43 years (s.d. 12). The controls were matched to probands for age, sex and ethnicity from more than 700 blood donors.

Published primers for the CAG repeat corresponding to the CHLC marker GTC10H06 (Gastier, J. M., et al., Genomics 32:78-85, 1996) were purchased form Gibco BRL (Paisley, Scotland). PCR was carried out using high molecular weight genomic DNA isolated from lymphocytes by phenol/chloroform extraction. Reproducible amplification was achieved using an MJ PTC 110-96 VH thermocycler. The following protocol was utilized: denaturation at 94° C. for 5 min., followed by an initial cycle of 94° C. for 1 min., 65° C. for 2 min., and then 72° C. for 1 min. for primer annealing. The primer-annealing temperature was then reduced over the next 12 cycles by 0.5° C. per cycle to a final value of 59° C. This was followed by 22 cycles consisting of 94° C. for 30 seconds, 58° C. for 30 seconds, and 72° C. for 1 minute. Reactions were carried out in a volume of 12.5 µl of 1×PCR buffer containing 1.5 mM $MgCl_2$, 40 ng DNA, 0.6 µM primers (where the forward primes was 5' end labeled with $\gamma$-$^{32}$p DATP), 0.08 mM dNTPs and 0.5 U of Taq polymerase. PCR products were electrophoresed on 6% polyacrylamide gels, and used for autoradiographic analyses. Descriptive statistics for the allele distribution in schizophrenic subjects were as follows: mean repeat size 18.4 (s.d. 1.9), median 19, range 13-23. Results are shown in Table 5.

TABLE 5

Numbers of each size of allele in patients and controls (frequencies in brackets)

| Repeat number | Control | Schizophrenia |
| --- | --- | --- |
| 13 | 14 (0.038) | 21 (0.054) |
| 14 | 15 (0.041) | 6 (0.015) |
| 15 | 3 (0.008) | 3 (0.008) |
| 16 | 6 (0.016) | 13 (0.034) |
| 17 | 52 (0.142) | 39 (0.101) |
| 18 | 80 (0.219) | 89 (0.229) |
| 19 | 131 (0.358) | 129 (0.332) |
| 20 | 36 (0.098) | 52 (0.134) |
| 21 | 22 (0.060) | 24 (0.062) |
| 22 | 6 (0.016) | 8 (0.021) |
| 23 | 1 (0.003) | 0 |
| 24 | 0 | 3 (0.008) |
| 30 | 0 | 1 (0.003) |
| total | 366 | 388 |

When the alleles were dichotomized into $\leq 19$ and $>19$, schizophrenic probands had a higher frequency of alleles with >19 repeats than did controls ($\chi^2$=2.820, 1 d.f, P=0.047, 1-tail). However, a comparison of the allele frequency distributions did not meet conventional levels of significance (i.e., $P \leq 0.05$) (Mann-Whitney U=67440, W=134601, P=0.11 (1-tail)). No association was found between repeat size and gender in the schizophrenic samples, but a later age-at-onset was associated with larger allele size (Mann-Whitney U=2625.5, W=6084.5, P=0.046 (2-tail)), contrary to expectations.

The data provide support for an association between moderately large CAG repeats in the hKCa3/KCNN3 gene and schizophrenia. Although a lesser trend was found for larger repeats in this patient group under the comparison of the overall allele frequencies, dichotomization of the sample according to Chandy et al (Mol. Psych. 3:32-37, 1998), which was justified by the previous hypothesis, revealed a result that meets the convention criteria of $p \leq 0.05$.

Although a positive association between the length of the CAG trinucleotide repeat and schizophrenia was noted, it cannot be assumed that the polyglutamine sequence in the channel is directly involved in increased susceptibility in schizophrenia, although this is one hypothesis. It is possible that the polymorphic repeat is merely in linkage disequilibrium with a disease related polymorphism which lies elsewhere in the hKCa3/KCNN3 gene or in a neighboring gene.

Example 7

Transgenic Mice Expressing hKCa3/KCNN3

Transgenic mice that can produce hKCa3/KCNN3 are made according to methods well known in the art. For example, young female mice are injected with hormones to induce superovulation, and are mated. The one celled embryos are collected, and the pronuclei injected with a purified DNA solution containing the constructs which encode hKCa3/KCNN3. The injected eggs are cultured briefly, and re-implanted into pseudopregnant female mice. Genomic DNA is prepared from each progeny, and analyzed by PCR or Southern blot to determine the mouse's genotype. Mice who carry the transgene are subsequently mated in order to produce a line of mice.

Using these method mice are produced which contain transgenes encoding hKCa3/KCNN3. In order to target the expression to specific cell types, transgenic mice are produced which carry genes encoding hKCa3/KCNN3 under the control of specific promoters. Examples of such constructs are genes encoding SEQ ID NO:2 under the control of the neurofilament light promoter sequences (Charron, G., et al., *J. Biol. Chem.* 270:25739-25745, 1995), which specifically target the expression of hKCa3/KCNN3 to neurons.

Although the invention has been described with reference to the presently preferred embodiment, it should be understood that various modifications can be made without departing from the spirit of the invention. Accordingly, the invention is limited only by the following claims.

What is claimed is:

1. A substantially purified human small conductance calcium-activated channel-3 (hKCa3/KCNN3) polypeptide comprising an amino acid sequence as set forth in SEQ ID NO:2.

2. A composition comprising:
   (a) a substantially pure hKCa3/KCNN3 polypeptide comprising an amino acid sequence as set forth in SEQ ID NO: 2; and
   (b) a pharmaceutically acceptable carrier.

3. The composition of claim 2, wherein the carrier is a liposome.

4. The composition of claim 2, wherein the polypeptide is conjugated to a carrier protein.

5. The composition of claim 4, wherein the carrier protein is selected from the group consisting of keyhole limpet hemocyanin (KLH), thyroglobulin, bovine serum albumin (BSA), and tetanus toxoid.

* * * * *

SEQUENCE LISTING

<160> NUMBER OF SEQ ID NOS: 15

<210> SEQ ID NO 1
<211> LENGTH: 2521
<212> TYPE: DNA
<213> ORGANISM: Homo sapiens
<220> FEATURE:
<221> NAME/KEY: CDS
<222> LOCATION: (287)...(2479)

<400> SEQUENCE: 1

```
gcctcacacg ctcctagagg accacctcct gagagagttc tttcaccccc tcttctttct     60
ccaagctccc ctcctgctct ccctccctgc ccaatacaat gcattcttga gtggcagcgt    120
ctggactcca ggcagcccca gagaaccgaa gcaagccaaa gagaggactg gagccaagat    180
actggtgggg gagattggat gcctggcttt ctttgaggac atctttggag cgagggtggc    240
tttggggtgg gggcttgtgc tgcagggaat acagccaggc cccaag atg gac act        295
                                                    Met Asp Thr
                                                      1 tct ggg cac ttc cat gac tcg ggg gtg ggg gac ttg gat gaa gac ccc       343
Ser Gly His Phe His Asp Ser Gly Val Gly Asp Leu Asp Glu Asp Pro
  5                  10                  15 aag tgc ccc tgt cca tcc tct ggg gat gag cag cag cag cag cag cag       391
Lys Cys Pro Cys Pro Ser Ser Gly Asp Glu Gln Gln Gln Gln Gln Gln
 20                  25                  30                  35 cag caa cag cag cag cag cca cca ccg cca gcg tca cca gca gcc ccc       439
Gln Gln Gln Gln Gln Gln Pro Pro Pro Pro Ala Ser Pro Ala Ala Pro
                 40                  45                  50 cag cag ccc ctg gga ccc tcg ctg cag cct cag cct ccg cag ctt cag       487
Gln Gln Pro Leu Gly Pro Ser Leu Gln Pro Gln Pro Pro Gln Leu Gln
             55                  60                  65 cag cag cag cag cag cag cag cag cag cag cag cag tca ccg cat           535
Gln Gln Gln Gln Gln Gln Gln Gln Gln Gln Gln Gln Ser Pro His
         70                  75                  80 ccc ctg tct cag ctc gcc caa ctc cag agc cag ccc gtc cac cct ggc       583
Pro Leu Ser Gln Leu Ala Gln Leu Gln Ser Gln Pro Val His Pro Gly
     85                  90                  95 ctg ctg cac tcc tct ccc acc gct ttc agg gcc ccc cct tcg tcc aac       631
Leu Leu His Ser Ser Pro Thr Ala Phe Arg Ala Pro Pro Ser Ser Asn
100                 105                 110                 115 tcc acc gcc atc ctc cac cct tcc tcc agg caa ggc agc cag ctc aat       679
Ser Thr Ala Ile Leu His Pro Ser Ser Arg Gln Gly Ser Gln Leu Asn
                120                 125                 130 ctc aat gac cac ttg ctt ggc cac tct cca agt tcc aca gct aca agt       727
Leu Asn Asp His Leu Leu Gly His Ser Pro Ser Ser Thr Ala Thr Ser
            135                 140                 145 ggg cct ggc gga ggc agc cgg cac cga cag gcc agc ccc ctg gtg cac       775
Gly Pro Gly Gly Gly Ser Arg His Arg Gln Ala Ser Pro Leu Val His
        150                 155                 160 cgg cgg gac agc aac ccc ttc acg gag atc gcc atg agc tcc tgc aag       823
Arg Arg Asp Ser Asn Pro Phe Thr Glu Ile Ala Met Ser Ser Cys Lys
```

-continued

|     |     |     |     | 165 |     |     |     |     | 170 |     |     |     |     | 175 |     |      |
|-----|-----|-----|-----|-----|-----|-----|-----|-----|-----|-----|-----|-----|-----|-----|-----|------|
| tat | agc | ggt | ggg | gtc | atg | aag | ccc | ctc | agc | cgc | ctc | agc | gcc | tcc | cgg | 871  |
| Tyr | Ser | Gly | Gly | Val | Met | Lys | Pro | Leu | Ser | Arg | Leu | Ser | Ala | Ser | Arg |      |
| 180 |     |     |     |     | 185 |     |     |     |     | 190 |     |     |     |     | 195 |      | agg aac ctc atc gag gcc gag act gag ggc caa ccc ctc cag ctt ttc    919
Arg Asn Leu Ile Glu Ala Glu Thr Glu Gly Gln Pro Leu Gln Leu Phe
                    200                 205                 210 agc cct agc aac ccc ccg gag atc gtc atc tcc tcc cgg gag gac aac    967
Ser Pro Ser Asn Pro Pro Glu Ile Val Ile Ser Ser Arg Glu Asp Asn
                215                 220                 225 cat gcc cac cag acc ctg ctc cat cac cct aat gcc acc cac aac cac   1015
His Ala His Gln Thr Leu Leu His His Pro Asn Ala Thr His Asn His
            230                 235                 240 cag cat gcc ggc acc acc gcc agc agc acc acc ttc ccc aaa gcc aac   1063
Gln His Ala Gly Thr Thr Ala Ser Ser Thr Thr Phe Pro Lys Ala Asn
            245                 250                 255 aag cgg aaa aac caa aac att ggc tat aag ctg gga cac agg agg gcc   1111
Lys Arg Lys Asn Gln Asn Ile Gly Tyr Lys Leu Gly His Arg Arg Ala
260                 265                 270                 275 ctg ttt gaa aag aga aag cga ctg agt gac tat gct ctg att ttt ggg   1159
Leu Phe Glu Lys Arg Lys Arg Leu Ser Asp Tyr Ala Leu Ile Phe Gly
                    280                 285                 290 atg ttt gga att gtt gtt atg gtg ata gag acc gag ctc tct tgg ggt   1207
Met Phe Gly Ile Val Val Met Val Ile Glu Thr Glu Leu Ser Trp Gly
                295                 300                 305 ttg tac tca aag gac tcc atg ttt tcg ttg gcc ctg aaa tgc cgt atc   1255
Leu Tyr Ser Lys Asp Ser Met Phe Ser Leu Ala Leu Lys Cys Arg Ile
            310                 315                 320 agt ctg tcc acc atc atc ctt ttg ggc ttg atc atc gcc tac cac aca   1303
Ser Leu Ser Thr Ile Ile Leu Leu Gly Leu Ile Ile Ala Tyr His Thr
            325                 330                 335 cgt gga gtc cag ctc ttc gtg atc gac aac gac gcg gat gac tgg cgg   1351
Arg Gly Val Gln Leu Phe Val Ile Asp Asn Asp Ala Asp Asp Trp Arg
340                 345                 350                 355 ata gcc atg acc tac gag cgc atc ctc tac att agc ctg gag atg ctg   1399
Ile Ala Met Thr Tyr Glu Arg Ile Leu Tyr Ile Ser Leu Glu Met Leu
                    360                 365                 370 gtg tac aca aac cac acc att cct ggc gag tac aag ttc ttc tgg gcg   1447
Val Tyr Thr Asn His Thr Ile Pro Gly Glu Tyr Lys Phe Phe Trp Ala
                375                 380                 385 gca cgc ctg gcc ttc tcc tac aca ccc tcc cgg gcg gag gcc gat gtg   1495
Ala Arg Leu Ala Phe Ser Tyr Thr Pro Ser Arg Ala Glu Ala Asp Val
            390                 395                 400 gac atc atc ctg tct atc ccc atg ttc ctg cgc ctg tac ctg atc gcc   1543
Asp Ile Ile Leu Ser Ile Pro Met Phe Leu Arg Leu Tyr Leu Ile Ala
405                 410                 415 cga gtc atg ctg cta cac agc aag ctc ttc acc gat gcc tcg tcc cgc   1591
Arg Val Met Leu Leu His Ser Lys Leu Phe Thr Asp Ala Ser Ser Arg
420                 425                 430                 435 agc atc ggg gcc ctc aac aag atc aac ttc aac acc cgc ttt gtc atg   1639
Ser Ile Gly Ala Leu Asn Lys Ile Asn Phe Asn Thr Arg Phe Val Met
                440                 445                 450 aag acg ctc atg acc atc tgc cct ggc act gtg ctc ctc gtg ttc agc   1687
Lys Thr Leu Met Thr Ile Cys Pro Gly Thr Val Leu Leu Val Phe Ser
            455                 460                 465 atc tct ctg tgg atc att gct gcc tgg acc gtc cgt gtc tgt gaa agg   1735
Ile Ser Leu Trp Ile Ile Ala Ala Trp Thr Val Arg Val Cys Glu Arg
            470                 475                 480 tac cat gac cag cag gac gta act agt aac ttt ctg ggt gcc atg tgg   1783

```
Tyr His Asp Gln Gln Asp Val Thr Ser Asn Phe Leu Gly Ala Met Trp
    485                 490                 495 ctc atc tcc atc aca ttc ctt tcc att ggt tat ggg gac atg gtg ccc      1831
Leu Ile Ser Ile Thr Phe Leu Ser Ile Gly Tyr Gly Asp Met Val Pro
500                 505                 510                 515 cac aca tac tgt ggg aaa ggt gtc tgt ctc ctc act ggc atc atg ggt      1879
His Thr Tyr Cys Gly Lys Gly Val Cys Leu Leu Thr Gly Ile Met Gly
            520                 525                 530 gca ggc tgc act gcc ctt gtg gtg gcc gtg gtg gcc cga aag ctg gaa      1927
Ala Gly Cys Thr Ala Leu Val Val Ala Val Val Ala Arg Lys Leu Glu
        535                 540                 545 ctc acc aaa gcg gag aag cac gtg cat aac ttc atg atg gac act cag      1975
Leu Thr Lys Ala Glu Lys His Val His Asn Phe Met Met Asp Thr Gln
    550                 555                 560 ctc acc aag cgg atc aag aat gct gca gca aat gtc ctt cgg gaa aca      2023
Leu Thr Lys Arg Ile Lys Asn Ala Ala Ala Asn Val Leu Arg Glu Thr
565                 570                 575 tgg tta atc tat aaa cac aca aag ctg cta aag aag att gac cat gcc      2071
Trp Leu Ile Tyr Lys His Thr Lys Leu Leu Lys Lys Ile Asp His Ala
580                 585                 590                 595 aaa gtg agg aaa cac cag agg aag ttc ctc caa gct atc cac cag ttg      2119
Lys Val Arg Lys His Gln Arg Lys Phe Leu Gln Ala Ile His Gln Leu
                600                 605                 610 agg agc gtc aag atg gaa cag agg aag ctg agt gac caa gcc aac act      2167
Arg Ser Val Lys Met Glu Gln Arg Lys Leu Ser Asp Gln Ala Asn Thr
            615                 620                 625 ctg gtg gac ctt tcc aag atg cag aat gtc atg tat gac tta atc aca      2215
Leu Val Asp Leu Ser Lys Met Gln Asn Val Met Tyr Asp Leu Ile Thr
        630                 635                 640 gaa ctc aat gac cgg agc gaa gac ctg gag aag cag att ggc agc ctg      2263
Glu Leu Asn Asp Arg Ser Glu Asp Leu Glu Lys Gln Ile Gly Ser Leu
    645                 650                 655 gag tcg aag ctg gag cat ctc acc gcc agc ttc aac tcc ctg ccg ctg      2311
Glu Ser Lys Leu Glu His Leu Thr Ala Ser Phe Asn Ser Leu Pro Leu
660                 665                 670                 675 ctc atc gcc gac acc ctg cgc cag cag cag cag ctc ctg tct gcc          2359
Leu Ile Ala Asp Thr Leu Arg Gln Gln Gln Gln Gln Leu Leu Ser Ala
                680                 685                 690 atc atc gag gcc cgg ggt gtc agc gtg gca gtg ggc acc acc cac acc      2407
Ile Ile Glu Ala Arg Gly Val Ser Val Ala Val Gly Thr Thr His Thr
            695                 700                 705 cca atc tcc gat agc ccc att ggg gtc agc tcc acc tcc ttc ccg acc      2455
Pro Ile Ser Asp Ser Pro Ile Gly Val Ser Ser Thr Ser Phe Pro Thr
        710                 715                 720 ccg tac aca agt tca agc agt tgc taaataaatc tccccactcc agaagcatta    2509
Pro Tyr Thr Ser Ser Ser Ser Cys
    725                 730 aaaaaaaaaa aa                                                        2521

<210> SEQ ID NO 2
<211> LENGTH: 731
<212> TYPE: PRT
<213> ORGANISM: Homo sapiens

<400> SEQUENCE: 2

Met Asp Thr Ser Gly His Phe His Asp Ser Gly Val Gly Asp Leu Asp
1               5                   10                  15

Glu Asp Pro Lys Cys Pro Cys Pro Ser Ser Gly Asp Glu Gln Gln Gln
            20                  25                  30
```

-continued

```
Gln Gln Gln Gln Gln Gln Gln Gln Pro Pro Pro Ala Ser Pro
    35                  40              45

Ala Ala Pro Gln Gln Pro Leu Gly Pro Ser Leu Gln Pro Gln Pro Pro
    50              55                  60

Gln Leu Gln Gln Gln Gln Gln Gln Gln Gln Gln Gln Gln Gln Gln Gln
65                  70                  75                  80

Ser Pro His Pro Leu Ser Gln Leu Ala Gln Leu Gln Ser Gln Pro Val
                85                  90                  95

His Pro Gly Leu Leu His Ser Ser Pro Thr Ala Phe Arg Ala Pro Pro
            100                 105                 110

Ser Ser Asn Ser Thr Ala Ile Leu His Pro Ser Ser Arg Gln Gly Ser
            115                 120                 125

Gln Leu Asn Leu Asn Asp His Leu Leu Gly His Ser Pro Ser Ser Thr
    130                 135                 140

Ala Thr Ser Gly Pro Gly Gly Ser Arg His Arg Gln Ala Ser Pro
145             150                 155                 160

Leu Val His Arg Arg Asp Ser Asn Pro Phe Thr Glu Ile Ala Met Ser
                165                 170                 175

Ser Cys Lys Tyr Ser Gly Gly Val Met Lys Pro Leu Ser Arg Leu Ser
            180                 185                 190

Ala Ser Arg Arg Asn Leu Ile Glu Ala Glu Thr Glu Gly Gln Pro Leu
    195                 200                 205

Gln Leu Phe Ser Pro Ser Asn Pro Pro Glu Ile Val Ile Ser Ser Arg
    210                 215                 220

Glu Asp Asn His Ala His Gln Thr Leu Leu His His Pro Asn Ala Thr
225                 230                 235                 240

His Asn His Gln His Ala Gly Thr Thr Ala Ser Ser Thr Thr Phe Pro
                245                 250                 255

Lys Ala Asn Lys Arg Lys Asn Gln Asn Ile Gly Tyr Lys Leu Gly His
            260                 265                 270

Arg Arg Ala Leu Phe Glu Lys Arg Lys Arg Leu Ser Asp Tyr Ala Leu
    275                 280                 285

Ile Phe Gly Met Phe Gly Ile Val Val Met Val Ile Glu Thr Glu Leu
290                 295                 300

Ser Trp Gly Leu Tyr Ser Lys Asp Ser Met Phe Ser Leu Ala Leu Lys
305                 310                 315                 320

Cys Arg Ile Ser Leu Ser Thr Ile Ile Leu Leu Gly Leu Ile Ile Ala
                325                 330                 335

Tyr His Thr Arg Gly Val Gln Leu Phe Val Ile Asp Asn Asp Ala Asp
            340                 345                 350

Asp Trp Arg Ile Ala Met Thr Tyr Glu Arg Ile Leu Tyr Ile Ser Leu
    355                 360                 365

Glu Met Leu Val Tyr Thr Asn His Thr Ile Pro Gly Glu Tyr Lys Phe
    370                 375                 380

Phe Trp Ala Ala Arg Leu Ala Phe Ser Tyr Thr Pro Ser Arg Ala Glu
385                 390                 395                 400

Ala Asp Val Asp Ile Ile Leu Ser Ile Pro Met Phe Leu Arg Leu Tyr
                405                 410                 415

Leu Ile Ala Arg Val Met Leu His Ser Lys Leu Phe Thr Asp Ala
            420                 425                 430

Ser Ser Arg Ser Ile Gly Ala Leu Asn Lys Ile Asn Phe Asn Thr Arg
    435                 440                 445

Phe Val Met Lys Thr Leu Met Thr Ile Cys Pro Gly Thr Val Leu Leu
```

|  | 450 |  | 455 |  | 460 |  |

Val Phe Ser Ile Ser Leu Trp Ile Ile Ala Ala Trp Thr Val Arg Val
465      470      475      480

Cys Glu Arg Tyr His Asp Gln Gln Asp Val Thr Ser Asn Phe Leu Gly
      485      490      495

Ala Met Trp Leu Ile Ser Ile Thr Phe Leu Ser Ile Gly Tyr Gly Asp
    500      505      510

Met Val Pro His Thr Tyr Cys Gly Lys Gly Val Cys Leu Leu Thr Gly
    515      520      525

Ile Met Gly Ala Gly Cys Thr Ala Leu Val Val Ala Val Val Ala Arg
530      535      540

Lys Leu Glu Leu Thr Lys Ala Glu Lys His Val His Asn Phe Met Met
545      550      555      560

Asp Thr Gln Leu Thr Lys Arg Ile Lys Asn Ala Ala Ala Asn Val Leu
      565      570      575

Arg Glu Thr Trp Leu Ile Tyr Lys His Thr Lys Leu Leu Lys Lys Ile
    580      585      590

Asp His Ala Lys Val Arg Lys His Gln Arg Lys Phe Leu Gln Ala Ile
    595      600      605

His Gln Leu Arg Ser Val Lys Met Glu Gln Arg Lys Leu Ser Asp Gln
    610      615      620

Ala Asn Thr Leu Val Asp Leu Ser Lys Met Gln Asn Val Met Tyr Asp
625      630      635      640

Leu Ile Thr Glu Leu Asn Asp Arg Ser Glu Asp Leu Glu Lys Gln Ile
      645      650      655

Gly Ser Leu Glu Ser Lys Leu Glu His Leu Thr Ala Ser Phe Asn Ser
    660      665      670

Leu Pro Leu Leu Ile Ala Asp Thr Leu Arg Gln Gln Gln Gln Gln Leu
    675      680      685

Leu Ser Ala Ile Ile Glu Ala Arg Gly Val Ser Val Ala Val Gly Thr
    690      695      700

Thr His Thr Pro Ile Ser Asp Ser Pro Ile Gly Val Ser Ser Thr Ser
705      710      715      720

Phe Pro Thr Pro Tyr Thr Ser Ser Ser Cys
    725      730

<210> SEQ ID NO 3
<211> LENGTH: 15
<212> TYPE: DNA
<213> ORGANISM: Homo sapiens

<400> SEQUENCE: 3
tttttctttt tttcg      15

<210> SEQ ID NO 4
<211> LENGTH: 72
<212> TYPE: DNA
<213> ORGANISM: Homo sapiens

<400> SEQUENCE: 4
nnnctncagc agcagcagca gtcnnnnann nnnnnnnnn nnnnnnnnnn nnnnnnnnnn  60
aanannncan nc      72

<210> SEQ ID NO 5
<211> LENGTH: 2526
<212> TYPE: DNA

<213> ORGANISM: Homo sapiens

<400> SEQUENCE: 5

```
gcctggcctc acacgctcct agaggaccac ctcctgagag agttctttca cccctcttc      60
tttctccaag ctcccctcct gctctccctc cctgcccaat acaatgcatt cttgagtggc    120
agcgtctgga ctccaggcag ccccagagaa ccgaagcaag ccaaagagag gactggagcc    180
aagatactgg tgggggagat tggatgcctg gctttctttg aggacatctt tggagcgagg    240
gtggctttgg ggtgggggct tgtgctgcag ggaatacagc caggcccaa gatggacact     300
tctgggcact tccatgactc gggggtgggg gacttggatg aagaccccaa gtgcccctgt    360
ccatcctctg gggatgagca gcagcagcag cagcagcagc aacagcagca gcagccacca    420
ccgccagcgt caccagcagc cccccagcag ccctgggac cctcgctgca gcctcagcct     480
ccgcagcttc agcagcagca gcagcagcag cagcagcagc agcagcagca gtcaccgcat    540
cccctgtctc agctcgccca actccagagc cagcccgtcc accctggcct gctgcactcc    600
tctcccaccg ctttcagggc ccccccttcg tccaactcca ccgccatcct ccacccttcc    660
tccaggcaag gcagccagct caatctcaat gaccacttgc ttggccactc tccaagttcc    720
acagctacaa gtgggcctgg cggaggcagc cggcaccgac aggccagccc cctggtgcac    780
cggcgggaca gcaacccctt cacggagatc gccatgagct cctgcaagta tagcggtggg    840
gtcatgaagc ccctcagccg cctcagcgcc tcccggagga acctcatcga ggccgagact    900
gagggccaac ccctccagct tttcagccct agcaacccc cggagatcgt catctcctcc     960
cgggaggaca accatgccca ccagaccctg ctccatcacc ctaatgccac ccacaaccac   1020
cagcatgccg gcaccaccgc cagcagcacc accttcccca agccaacaa gcggaaaaac   1080
caaaacattg gctataagct gggacacagg agggccctgt ttgaaaagag aaagcgactg   1140
agtgactatg ctctgatttt tgggatgttt ggaattgttg ttatggtgat agagaccgag   1200
ctctcttggg gtttgtactc aaaggactcc atgttttcgt tggccctgaa atgccgtatc   1260
agtctgtcca ccatcatcct tttgggcttg atcatcgcct accacacacg tggagtccag   1320
ctcttcgtga tcgacaacga cgcggatgac tggcggatag ccatgaccta cgagcgcatc   1380
ctctacatta gcctggagat gctggtgtac acaaaccaca ccattcctgg cgagtacaag   1440
ttcttctggg cggcacgcct ggccttctcc tacacaccct cccgggcgga ggccgatgtg   1500
gacatcatcc tgtctatccc catgttcctg cgcctgtacc tgatcgcccg agtcatgctg   1560
ctacacagca agctcttcac cgatgcctcg tcccgcagca tcggggccct caacaagatc   1620
aacttcaaca cccgctttgt catgaagacg ctcatgacca tctgccctgg cactgtgctg   1680
ctcgtgttca gcatctctct gtggatcatt gctgcctgga ccgtccgtgt ctgtgaaagg   1740
taccatgacc agcaggacgt aactagtaac tttctgggtg ccatgtggct catctccatc   1800
acattccttt ccattggtta tggggacatg gtgcccaca catactgtgg gaaaggtgtc   1860
tgtctcctca ctggcatcat gggtgcaggc tgcactgccc ttgtggtggc cgtggtggcc   1920
cgaaagctgg aactcaccaa agcggagaag cacgtgcata acttcatgat ggacactcag   1980
ctcaccaagc ggatcaagaa tgctgcagca aatgtccttc gggaaacatg gttaatctat   2040
aaacacacaa agctgctaaa gaagattgac catgccaaag tgaggaaaca ccagaggaag   2100
ttcctccaag ctatccacca gttgaggagc gtcaagatgg aacagaggaa gctgagtgac   2160
caagccaaca ctctggtgga cctttccaag atgcagaatg tcatgtatga cttaatcaca   2220
gaactcaatg accggagcga agacctggag aagcagattg gcagcctgga gtcgaagctg   2280
```

```
gagcatctca ccgccagctt caactccctg ccgctgctca tcgccgacac cctgcgccag      2340
cagcagcagc agctcctgtc tgccatcatc gaggcccggg gtgtcagcgt ggcagtgggc      2400
accacccaca ccccaatctc cgatacgccc attggggtca gctccacctc cttcccgacc      2460
ccgtacacaa gttcaagcag ttgctaaata atctccccca ctccagaagc attaaaaaaa      2520
aaaaaa                                                                 2526
```

<210> SEQ ID NO 6
<211> LENGTH: 159
<212> TYPE: DNA
<213> ORGANISM: Rattus rattus

<400> SEQUENCE: 6

```
actatcctca taattccttt ggagtttagc ttagaattgt atcggctcaa ctatcttcta       60
tgaaacggaa ctgaagctca ttgcatcacc cccgccctac gtaccgggct aaccatcaag      120
catggcatta tggtcctcgc tcatgaattc ctatttcag                             159
```

<210> SEQ ID NO 7
<211> LENGTH: 217
<212> TYPE: DNA
<213> ORGANISM: Rattus rattus

<400> SEQUENCE: 7

```
cgt ctt caa acc cag tga gcc tct cag cag cag cag cag gct ctc ctg        48 ttt ttt gta ata gag ctg gta tac ata tcc tca taa ttc ctt tgg agt        96 tta gct tag aat tgt atc ggc tca act atc ttc tat gaa acg ggc tga       144 agc tca ttg cat cac ccc cgc cct acg tac cgg gct aac cat caa gca       192 tgg cat tat ggt cct cgc tca taa a                                    217
```

<210> SEQ ID NO 8
<211> LENGTH: 44
<212> TYPE: PRT
<213> ORGANISM: Rattus rattus

<400> SEQUENCE: 8

Glu Ser Pro Val Pro Leu Gln Gln Gln Gln Ala Pro Leu Pro Val
1               5                   10                  15

Asn Ala Val Val Asn Leu Pro Ile Gly Leu Glu Gly Cys Ala Ile Pro
            20                  25                  30

Thr His Gly Thr Phe Val Ile Ser Ala Pro Ser Ile
        35                  40

<210> SEQ ID NO 9
<211> LENGTH: 8
<212> TYPE: PRT
<213> ORGANISM: Homo sapiens

<400> SEQUENCE: 9

Thr Xaa Xaa Thr Xaa Gly Tyr Gly
1               5

<210> SEQ ID NO 10
<211> LENGTH: 23
<212> TYPE: DNA
<213> ORGANISM: Homo sapiens

<400> SEQUENCE: 10

```
acccccaagtg ccctgtcca tcc                                          23

<210> SEQ ID NO 11
<211> LENGTH: 24
<212> TYPE: DNA
<213> ORGANISM: Homo sapiens

<400> SEQUENCE: 11
atctccgtga aggggttgct gtcc                                         24

<210> SEQ ID NO 12
<211> LENGTH: 24
<212> TYPE: DNA
<213> ORGANISM: Homo sapiens

<400> SEQUENCE: 12
ctgaaagcgg tgggagagga gtgc                                         24

<210> SEQ ID NO 13
<211> LENGTH: 25
<212> TYPE: DNA
<213> ORGANISM: Homo sapiens

<400> SEQUENCE: 13
caccgtcagt gtcaccagta gtccc                                        25

<210> SEQ ID NO 14
<211> LENGTH: 21
<212> TYPE: DNA
<213> ORGANISM: Homo sapiens

<400> SEQUENCE: 14 gcagccctg ggaccctcgc t                                             21

<210> SEQ ID NO 15
<211> LENGTH: 26
<212> TYPE: DNA
<213> ORGANISM: Homo sapiens

<400> SEQUENCE: 15
acatgtagct gtggaacttg gagagt                                       26
```